US010986992B2

(12) United States Patent
Miller et al.

(10) Patent No.: US 10,986,992 B2
(45) Date of Patent: Apr. 27, 2021

(54) DYNAMIC DISPLAY SYSTEM AND METHOD FOR CUSTOMIZING A CONTROLLER IN A DISPLAY SYSTEM

(71) Applicant: Massachusetts Institute of Technology, Cambridge, MA (US)

(72) Inventors: Earl Keith Miller, Somerville, MA (US); Timothy Joseph Buschman, Haddonfield, NJ (US); Simon John Kornblith, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 566 days.

(21) Appl. No.: 15/679,126

(22) Filed: Aug. 16, 2017

(65) Prior Publication Data
US 2018/0049636 A1 Feb. 22, 2018

Related U.S. Application Data

(60) Provisional application No. 62/376,132, filed on Aug. 17, 2016.

(51) Int. Cl.
*A61B 3/00* (2006.01)
*G09B 19/00* (2006.01)
(Continued)

(52) U.S. Cl.
CPC ............ *A61B 3/0041* (2013.01); *A61B 3/10* (2013.01); *A61B 5/0059* (2013.01);
(Continued)

(58) Field of Classification Search
None
See application file for complete search history.

(56) References Cited

U.S. PATENT DOCUMENTS 9,927,940 B2    3/2018  Miller et al.
2012/0308972 A1 12/2012  Miller et al.
(Continued)

FOREIGN PATENT DOCUMENTS

WO      2012/167123 A1   12/2012
WO   WO 2012/167123       12/2012

OTHER PUBLICATIONS

Arnal, L.H. et al., "Cortical oscillations and sensory predictions," Trends Cogn Sci., 16: 390-398, (2012).
(Continued)

*Primary Examiner* — James B Hull
(74) *Attorney, Agent, or Firm* — Hamilton, Brook, Smith & Reynolds, P.C.

(57) ABSTRACT

A method, or corresponding dynamic display system, for customizing a controller of a display system includes presenting a visual stimulus to a subject at at least one known location relative to the subject's eye gaze; measuring brain activity of the subject's left and right brain hemispheres in response to the subject's viewing of the stimulus; processing the measured brain activity to determine a frequency-dependent metric of the measured brain activity; assessing independent cognitive capacities of the subject's left and right brain hemispheres based on the frequency-dependent metric; and adjusting a function of the controller in the display system according to the assessed independent capacities, such as by adjusting the function to change a stimulus load in a visual hemifield according to the brain activity in the contralateral brain hemisphere. Example applications include head-up display (HUD), augmented reality (AR) or virtual reality (VR) display systems, and brain injury assessment systems.

18 Claims, 20 Drawing Sheets
(8 of 20 Drawing Sheet(s) Filed in Color)

(51) Int. Cl.
  A61B 5/055    (2006.01)
  A61B 5/0476   (2006.01)
  A61B 5/00     (2006.01)
  A61B 3/10     (2006.01)
  A61B 5/0484   (2006.01)
  A61B 8/06     (2006.01)
  A61B 8/08     (2006.01)
  A61B 5/04     (2006.01)
  A61B 5/048    (2006.01)

(52) U.S. Cl.
  CPC ........ *A61B 5/0476* (2013.01); *A61B 5/04842* (2013.01); *A61B 5/055* (2013.01); *A61B 5/6801* (2013.01); *A61B 5/7278* (2013.01); *A61B 5/048* (2013.01); *A61B 5/04009* (2013.01); *A61B 8/06* (2013.01); *A61B 8/0816* (2013.01); *G09B 19/00* (2013.01)

(56) References Cited

U.S. PATENT DOCUMENTS

2013/0060125 A1*  3/2013  Zeman ............... A61B 5/048
                                              600/409
2015/0080753 A1*  3/2015  Miyazaki ............. G16H 40/63
                                              600/544

OTHER PUBLICATIONS

Asaad, W.F. et al., "A flexible software tool for temporally-precise behavioral control in Matlab." J. Neurosci Methods, 174: 245-258, (2008).
Asanuma, C. et al., "The thalamic relations of the caudal inferior parietal lobule and the lateral prefrontal cortex in monkeys: Divergent cortical projections from cell clusters in the medial pulvinar nucleus," J Comp Neurol., 241: 357-381, (1985).
Bastos, A.M. et al., "Visual areas exert feedforward and feedback influences through distinct frequency channels," Neuron, 85: 390-401, (2015).
Bays, P.M. et al., "Dynamic shifts of limited working memory resources in human vision," Science, 321: 851-854, (2008).
Bender DB., Retinotopic organization of macaque pulvinar, J Neurophysiol. 46: 672-693, (1984).
Buschman, T.J. et al., "Synchronous oscillatory neural ensembles for rules in the prefrontal cortex," Neuron, 76: 838-846 (2012).
Buschman, T.J. et al., "Serial, covert shifts of attention during visual search are reflected by the frontal eye fields and correlated with population oscillations," Neuron, 63: 386-396 (2009).
Buschman, T.J. et al., "Top-down versus bottom-up control of attention in the prefrontal and posterior parietal cortices," Science, 315: 1860-1862, (2007).
Buschman, T.J. et al., "Neural substrates of cognitive capacity limitations," Proc Natl Acad Sci., 108:11252-11255 (2011).
Engel, A.K. et al., "Beta-band oscillations—signalling the status quo?," Curr Opin Neurobiol, Cognitive neuroscience, 20:156-165, (2010).
Engel, A.K. et al., "Dynamic predictions: Oscillations and synchrony in top-down processing," Nat Rev Neurosci., 2: 704-716, (2001).
Fries, P. et al., "The effects of visual stimulation and selective visual attention on rhythmic neuronal synchronization in macaque area V4," J Neurosci., 28: 4823-4835, (2008).
Gray, C.M. et al., "Oscillatory responses in cat visual cortex exhibit inter-columnar synchronization which reflects global stimulus properties," Nature, 338: 334-337 (1989).
Gregoriou ,G.G. et al., "High-Frequency, Long-Range Coupling Between Prefrontal and Visual Cortex During Attention," Science, 324:1207-1210 (2009).
Gregoriou, G.G. et al. "Lesions of prefrontal cortex reduce attentional modulation of neuronal responses and synchrony in V4," Nat Neurosci., 17: 1003-1011 (2014).
Hipp, J.F. et al., "Oscillatory synchronization in large-scale cortical networks predicts perception," Neuron, 69: 387-396 (2011).
Howard, M.W. et al., "Gamma oscillations correlate with working memory load in humans" Cereb Cortex, 13: 1369-1374 (2003).
Ikkai, A. et al., "Contralateral delay activity provides a neural measure of the Number of representations in visual working memory," J Neurophysiol, 103: 1963-1968 (2010).
Jensen, O. et al., "Frontal theta activity in humans increases with memory load in a working memory task," Eur J Neurosci., 15: 1395-1399 (2002).
Kornblith, S. et al., "Stimulus Load and Oscillatory Activity in Higher Cortex, Cerebral Cortex," vol. 26, Issue 9,Sep. 1, 2016, published online Aug. 18, 2015, https://doi.org/10.1093/cercor/bhv182, pp. 3772-3784.
Kowalska, D.M. et al., "The role of the inferior prefrontal convexity in performance of delayed nonmatching-to-sample," Neuropsychologia, 29: 583-600 (1991).
Lara, A.H. et al., "Executive control processes underlying multi-item working memory," Nat Neurosci., advance online publication (2014).
Li, C-SR et al., "Effect of reversible inactivation of macaque lateral intraparietal area on visual and memory saccades," J Neurophysiol, 81: 1827-1838 (1999).
Linden, DEJ et al., "Cortical capacity constraints for visual working memory: dissociation of fMRI load effects in a fronto-parietal network," NeuroImage, 20: 1518-1530 (2003).
Lisman, J.E. et al., "Storage of 7 +-31 2 short-term memories in oscillatory subcycles," Science, 3. 267: 1512-1515 (1995).
Luck, S.J. et al., "The capacity of visual working memory for features and conjunctions," Nature, 390: 279-280 (1997).
Luck, S.J. et al., "Visual working memory capacity: from psychophysics and neurobiology to individual differences," Trends Cogn Sci., 17: 391-400 (2013).
Lundqvist, M. et al., "Theta and gamma power increases and alpha/beta power decreases with memory load in an attractor network model," J Cogn Neurosci., 23: 3008-3020 (2011).
Luria, R. et al., "Shape and color conjunction stimuli are represented as bound objects in visual working memory," Neuropsychologia, Attention and Short-Term Memory, 49: 1632-1639 (2011).
Matsushima, A. et al., "Different neuronal computations of spatial working memory for multiple locations within versus across visual hemifields," J Neurosci., 34: 5621-5626 (2014).
Ma, W.J. et al., "Changing concepts of working memory," Nat Neurosci., 17: 347-356 (2014).
McCollough, A.W. et al., "Electrophysiological measures of maintaining representations in visual working memory," Cortex, 43: 77-94 (2007).
Meltzer, J.A. et al., "Effects of Working Memory Load on Oscillatory Power in Human Intracranial EEG," Cereb Cortex, 18: 1843-1855 (2008).
Mitchell, D.J. et al, "The temporal evolution of electromagnetic markers sensitive to the capacity limits of visual short-term memory," Front Hum Neurosci., 5: 18 (2011).
Mittlböck, M. et al., "Measures of explained variation in gamma regression models," Commun Stat—Simul Comput., 31: 61-73 (2002).
Palva, J.M. et al., "Neuronal synchrony reveals working memory networks and predicts individual memory capacity" Proc Natl Acad Sci., 107:7580-7585 (2010).
Palva, S. et al., "Localization of cortical phase and amplitude dynamics during visual working memory encoding and retention," J Neurosci., 31: 5013-5025 (2011).
Passingham, R., "Delayed matching after selective prefrontal lesions in monkeys (*Macaca mulatta*)," Brain Res., 92: 89-102 (1975).
Pereira, J. et al., "A tradeoff between accuracy and flexibility in a working memory circuit endowed with slow feedback mechanisms," Cereb Cortex, in press:bhu202. (2014).
Richter, C.G. et al., "A jackknife approach to quantifying single-trial correlation between covariance-based metrics undefined on a single-trial basis," NeuroImage., 114:,57-70 (2015).

(56) References Cited

OTHER PUBLICATIONS

Saalmann, Y.B. et al., "The Pulvinar Regulates Information Transmission Between Cortical Areas Based on Attention Demands," Science, 337: 753-756 (2012).

Salazar, R.F. et al., "Content-specific fronto-parietal synchronization during visual working memory," Science, 338: 1097-1100 (2012).

Sawaguchi, T. et al., "D1 dopamine receptors in prefrontal cortex: involvement in working memory," Science, 251: 947-950 (1991).

Siegel, M. et al., "Neuronal synchronization along the dorsal visual pathway reflects the focus of spatial attention," Neuron, 60: 709-719 (2008).

Todd, J.J. et al., "Capacity limit of visual short-term memory in human posterior parietal cortex," Nature, 428: 751-754 (2004).

Todd, J.J. et al., "Posterior parietal cortex activity predicts individual differences in visual short-term memory capacity," Cogn Affect Behav Neurosci., 5: 144-155 (2005).

Vinck, M. et al., "The pairwise phase consistency: A bias-free measure of rhythmic neuronal synchronization.," NeuroImage, 51: 112-122 (2010).

Vogel, E.K. et al., "Neural activity predicts individual differences in visual working memory capacity," Nature, 428: 748-751 (2004).

Vogel, E.K. et al., "Neural measures reveal individual differences in controlling access to working memory," Nature, 438: 500-503 (2005).

Vogel, E.K. et al., "Storage of features, conjunctions, and objectsw in visual working memory," J Exp Psychol Hum Percept Perform, 27: 97-114 (2001).

Voytek, B. et al., "Prefrontal cortex and basal ganglia contributions to visual working memory," Proc Natl Acad Sci., 107: 18167-18172 (2010).

Wikipedia, "Functional neuroimaging," retrieved from https://en.wikipedia.org/wiki/Functional_neuroimaging, (Aug. 8, 2016).

Wikipedia, "Magnetoencephalography," retrieved from https://en.wikipedia.org/wiki/Magnetoencephalography, (Aug. 8, 2016).

Womelsdorf, T. et al., "Gamma-band synchronization in visual cortex predicts speed of change detection," Nature, 439: 733 (2006).

\* cited by examiner

DYNAMIC DISPLAY SYSTEM AND METHOD FOR CUSTOMIZING A CONTROLLER IN A DISPLAY SYSTEM

RELATED APPLICATION(S)

This application claims the benefit of U.S. Provisional Application No. 62/376,132, filed on Aug. 17, 2016. The entire teachings of the above application are incorporated herein by reference.

GOVERNMENT SUPPORT

This invention was made with Government support under Grant No. RO1 MH091174 awarded by the National Institutes of Health. The Government has certain rights in this invention.

BACKGROUND

The amount of information a person can process from a display, such as a computer display, head-up display, head mounted display, or television monitor, can be limited because conventional displays do not account for cognitive capacity limits in the person's visual hemispheres. Often, conventional displays are unbalanced or present too much information.

SUMMARY OF THE INVENTION

Embodiments of the present invention generally relate to display systems and methods and apparatus for customizing a controller in a display system. Embodiments include technology and techniques to use neurophysiologically determined feedback to measure independent cognitive capacities of the right and left halves of the brain.

A method for customizing a controller in a display system includes presenting a visual stimulus to a subject at at least one known location relative to the subject's eye gaze, and measuring brain activity of the subject's left and right brain hemispheres in response to the subject's viewing of the stimulus displayed. The brain activity has a frequency component associated therewith. The method further includes processing the measured brain activity to determine a frequency-dependent metric of the brain activity and assessing independent cognitive capacities of the subject's left and right brain hemispheres based on the frequency-dependent metric of the brain activity. A function of the controller in the display is adjusted according to the assessment of the independent cognitive capacities.

It should be understood that the term "stimulus" as used herein may include multiple visual (e.g., graphical) representations; thus, "stimulus" should be treated as interchangeable with "stimuli" where not explicitly limited to a singular visual representation.

Adjusting the function of the controller can include dynamically adjusting the function to change a property of the stimulus displayed and/or other visual representations displayed according to the assessment of the independent cognitive capacities. A property of the stimulus can be a location, size, quantity, color, speed of movement of the stimulus, or other property capable of being modified for display.

Adjusting the function to change the property of the stimulus being displayed can include adjusting the function to change a stimulus load in a visual hemifield according to the measured brain activity (e.g., the frequency-dependent metric) in the subject's contralateral brain hemisphere. Stimulus load may be adjusted (e.g., changed) by modulating at least one of a number of objects or a complexity of objects in the stimulus display.

The method can further include monitoring the subject's eye gaze by tracking the subject's eye position, for example, to ensure the subject subject's eye gaze is centered on the display, e.g., on a fixation point of the display. The method can include ensuring alignment of the subject's eye gaze with a fixation point during measuring of the brain activity, for example, by providing feedback to the subject, by moving the stimulus display in response to the subject's gaze, or both.

Measuring brain activity can include measuring at least one of EEG signals, MEG signals, infrared signals recorded from the scalp, BOLD signals from fMRI, and cerebral blood volume changes from functional ultrasound.

Measuring brain activity can include measuring local field potentials (e.g., by measuring EEG or MEG signals).

Processing the measured brain activity can include computing oscillatory power of the measured brain activity, such as local field potentials. The computed oscillatory power can be compared to a threshold value, and a compensatory action can be taken based on a result of the comparison. For example, the compensatory action can include, for a given brain hemisphere, modulating stimulus load to the contralateral visual hemifield. The oscillatory power can be computed for one or more selected frequency bands. The frequency bands can include a lower frequency band of about 8-50 Hz and a higher (upper) frequency band of about 50 Hz and above and up to about 200 Hz, e.g., about 50-100 Hz. A ratio of the oscillatory power in the higher frequency band to the oscillatory power in the lower frequency band can be computed. In a particular embodiment, the oscillatory power in the gamma band (e.g., high gamma band), which is about 50-100 Hz as known in the art, is analyzed.

The method can further include assessing the subject's current level of cognitive function by determining overall cognitive capacity of the subject as a function of the independent cognitive capacities. Assessing the subject's current level of cognitive function can include comparing the determined overall cognitive capacity to a baseline capacity.

A dynamic display system includes a display device to present a visual stimulus to a subject and a controller coupled to the display device. The controller causes the display device to display the visual stimulus at at least one known location relative to the subject's eye gaze. The display system further includes a detector to measure brain activity of the subject's left and right brain hemispheres in response to the subject's viewing of the stimulus. The brain activity has a frequency component associated therewith. The system includes at least one processor coupled to the detector and configured to process the measured brain activity to determine a frequency-dependent metric of the brain activity, assess independent cognitive capacities of the subject's left and right brain hemispheres based on the frequency-dependent metric of the brain activity, and adjust a function of the controller according to the assessment of the independent cognitive capacities.

The processor of the display system can be coupled to the display device directly or indirectly via the controller. The processor can be configured to adjust dynamically the function of the controller to change a property of the stimulus displayed according to the assessment of the independent capacities. Other visual representations can also be changed by the controller. The function of the controller can be adjusted, and, consequently a stimulus displayed can be adjusted, by adjusting a stimulus load in a visual hemifield according to the measured brain activity in the subject's contralateral brain hemisphere. The processor can be configured to adjust the function to change the stimulus load by modulating at least one of number of objects and complexity of objects in the stimulus display.

The display system can include a gaze monitor (e.g., a camera) that is configured to track the subject's eye position to monitor the subject's eye gaze. The stimulus can be displayed based on the subject's eye gaze.

The detector of the display system can be configured to measure local field potentials, and the processor can be configured to process the measured brain activity by computing oscillatory power of the measured local field potentials. The processor of the display system can be configured to compare the computed oscillatory power to a threshold value and take a compensatory action based on a result of the comparison. For example, the compensatory action can include, for a given brain hemisphere, modulating a stimulus load to the contralateral hemifield. The processor can be configured to compute oscillatory power for selected frequency bands, the frequency bands including a lower frequency band of about 8-50 Hz and a higher frequency band of about 50-200 Hz.

The display system can include at least one filter to condition the measured brain activity. The filter may be implemented in the detector, the processor, or both.

The controller of the display system is customizable. It can be implemented in hardware and configured to perform the functions described herein. Alternatively, the controller can be implemented in software. The customizable controller can be configured to perform the processing of the measured brain activity. Further, the controller can operate in a training mode and in an operational mode, where the operational mode may operate using parameters resulting from the training that occurred while in the training mode. Parameter optimization may occur in the operational mode.

A system for assessing brain injury includes a display device to display a visual stimulus to a subject, and a detector to measure brain activity of the subject's left and right brain hemispheres in response to the subject's viewing of the stimulus, the brain activity having a frequency component associated therewith. The system further includes at least one processor coupled to the detector and configured to process the measured brain activity to determine a frequency-dependent metric of the brain activity, assess independent cognitive capacities of the subject's left and right brain hemispheres based on the frequency-dependent metric of the brain activity, and output an indication of brain injury as a function of the assessment of the independent cognitive capacities. The indication of brain injury can be a measure of the likelihood that the subject has suffered a concussion, for example.

The display device, the detector, or both can be integrated into a wearable device, such as a helmet-style device or a smart phone device.

A method for assessing cognitive brain capacity includes presenting a visual stimulus to a subject; measuring brain activity of the subject's left and right brain hemispheres in response to the stimulus displayed, the brain activity having a frequency component associate therewith; processing the measured brain activity to determine a frequency-dependent metric of the brain activity; and assessing independent cognitive capacities of the subject's left and right brain hemispheres based on the frequency-dependent metric of the brain activity.

The method for assessing cognitive brain capacity can further include dynamically adjusting the stimulus displayed and/or other visual representations displayed according to the assessment of the independent cognitive capacities. Adjusting the stimulus displayed can include adjusting a stimulus load in a visual hemifield according to the measured brain activity (e.g., the frequency-dependent metric) in the subject's contralateral brain hemisphere. Stimulus load may be adjusted by modulating at least one of a number of objects or a complexity of objects in the stimulus display. The method can further include monitoring the subject's eye gaze by tracking the subject's eye position, for example, to ensure the subject subject's eye gaze is centered on the display, e.g., on a fixation point of the display.

A dynamic display system includes a display device to present a visual stimulus to a subject at at least one known location relative to the subject's eye gaze, and a detector to measure brain activity of the subject's left and right brain hemispheres in response to the subject's viewing of the stimulus. The brain activity can have a frequency component associated therewith. The system further includes at least one processor coupled to the detector and configured to process the measured brain activity to determine a frequency-dependent metric of the brain activity, and assess independent cognitive capacities of the subject's left and right brain hemispheres based on the frequency-dependent metric of the brain activity.

Advantages and Improvements

A limitation of the prior behavioral performance measure is that it requires multiple observations (trials) to gain an assessment of cognitive load and capacity. This can introduce delays of 5-10 minutes before a measure of capacity is available. Furthermore, capacity can change over time, for example, as a result of fatigue, stress, or other mental and environmental factors. The new technology described herein uses frequency-dependent brain measures that provide instantaneous feedback on load and capacity. This allows faster assessment as well as on-the-fly adjustments in ongoing task demands. The instantaneous feedback opens up new opportunities that could not be realized from previous systems. On-the-fly adjustment(s) can allow faster and better training for each individual to deal with the individual's capacity limits, as well as the possibility of dynamic displays that adjust themselves to reflect the instantaneous capacity of each individual over time (because capacity can fluctuate over time).

Commercial applications of assessing brain capacity based on frequency-dependent brain measures include, among others:

1. Training methods for improving cognitive bandwidth on each side of the brain using instantaneous feedback;

2. Dynamic display systems that change what is being displayed from moment-to-moment to account for changes in an individual's capacity over time;

3. Kits to test cognitive function, including a wearable brain sensor and display.

Embodiments can be used to improve performance in sports, law enforcement, and military. Sports teams may be arranged based on the team members' individual capacities. For example, members may be positioned on the right or left side of a field according to assessment of the members' right capacity vs. left capacity.

Furthermore, assessment of capacity based on frequency-dependent brain activity can be useful in identifying subpopulations in subjects, which currently cannot be done with behavioral test alone.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 12A shows percent power change for contralateral loads 1, 2, and 3 relative to the model intercept across frequencies and time. First dashed line indicates time of sample onset. Second dashed line indicates time of sample offset. FIG. 12B shows percent power change per contralateral stimulus. Boxes indicate significant modulations (bootstrap Z-test, $p<0.05$, Holm corrected for 22 frequencies×211 time points).

FIG. 13A shows percent power change for ipsilateral loads 1, 2, and 3 relative to the model intercept across frequencies and time. FIG. 13B shows percent power change per ipsilateral stimulus. Boxes indicate significant modulations (bootstrap Z-test, $p<0.05$, Holm corrected for 22 frequencies×211 time points).

DETAILED DESCRIPTION OF EMBODIMENTS THE INVENTION

Figure 1:
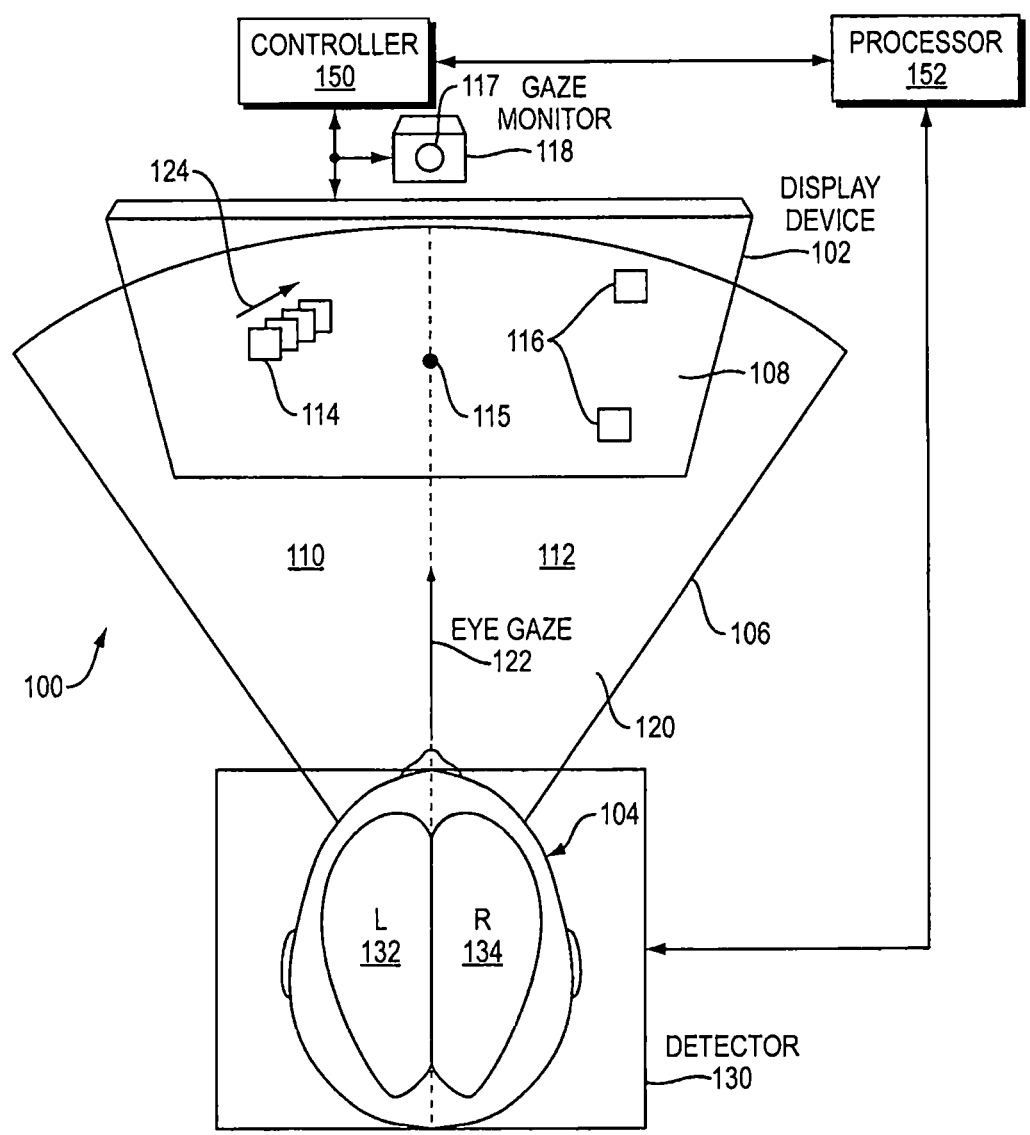
FIG. 1 is a schematic diagram illustrating a display system and method for customizing a controller of a display system including measuring brain activity of a subject's left and right brain hemispheres according to an example embodiment.

A description of example embodiments of the invention follows.

It has previously been shown that humans have independent cognitive capacities to process information on the left and right halves of visual space, i.e., in the right vs. left halves of the brain. A cognitive capacity test and example results have been described in an article by Buschman, T. J., et al., "Neural Substrates of Cognitive Capacity Limitations," PNAS Early Edition [online] Mar. 23, 2011, pp. 1-4, PNAS Jul. 5, 2011 Vol. 108 No. 27, pp. 11252-11255. The teachings of the article and supporting information are incorporated herein by reference in their entirety.

Applicant's previous approach of methods and systems for displaying information in a manner accounting for independent cognitive capacities in the right vs. left half of vision has been described in U.S. patent application Ser. No. 13/486,762, filed on Jun. 1, 2012 and published as Publication No. 2012/0308972 on Dec. 6, 2012, which is incorporated herein by reference in its entirety.

The previous approach describes a method and technology using behavioral performance measures to assess the independent visual capacities in the left vs right brain. This has a variety of real world applications including assessment of capacities to improve safety and effectiveness of military and law enforcement personal, individualized heads-up displays, etc.

The present approach involves the use of direct measures of brain activity to make the same assessment, but with greater accuracy. A recent publication (Kornblith S., et al., "Stimulus Load and Oscillatory Activity in Higher Cortex," Cerebral Cortex, Volume 26, Issue 9, 1 Sep. 2016, Pages 3772-3784, published online Aug. 18, 2015 (pp. 1-13)) has shown that specific bands of brain oscillations can be used to assess capacity in the separate visual hemifields, as further described in Example 6 below. Not any measure of neural activity will do. Applicant's new discovery shows that higher brain frequencies reflect the independent capacities in the right vs. left brain. By contrast, lower frequencies reflect overall capacity across the right and left. This can be exploited to gain accurate measures of how many stimuli are being processed in each half of the brain (via higher frequencies) and how this affects overall capacity (via lower frequencies). This provides useful insight above and beyond the assessment of capacity limits using the behavior measures in the previous approach.

Embodiments can include a camera to track subjects' eye movements, a computer monitor or other display device to present materials related to the cognitive test, and devices for measuring brain activity. The latter includes EEG, MEG, infrared recordings from the scalp, as well as BOLD signals from FMRI and functional ultrasound. A computer can be used to decode and assess cognitive capacity based on changes in neural activity as reflected in measured brain activity.

Embodiments may use functional neuroimaging to measure brain activity. Common methods of functional neuroimaging include positron emission tomography (PET), functional magnetic resonance imaging (fMRI), multichannel electroencephalography (EEG), magnetoencephalography (MEG), near infrared spectroscopic imaging (NIRSI), functional ultrasound, and single-photon emission computed tomography (SPECT) (See, for example, "Functional neuroimaging," Wikipedia, accessed Aug. 8, 2016). Functional ultrasound is a method for imaging transient changes in blood volume in the whole brain. It is thought to offer better spatiotemporal resolution of these transient changes than other functional brain imaging modalities.

Electroencephalography (EEG) is a neuroimaging technique to measure the electrical activity of the brain. Magnetoencephalography (MEG) is a neuroimaging technique that identifies brain activity by measuring magnetic field produced by small electrical currents arising from the neurons of the brain. MEG can be used to generate an accurate location of the magnetic fields produced by the neurons. MEG is useful for measuring time courses of activity. For example, MEG can resolve events with a precision of 10 milliseconds or faster, while functional MRI (fMRT), which depends on changes in blood flow, can at best resolve events with a precision of several hundred milliseconds. MEG can also pinpoint sources in primary auditory, somatosensory, and motor areas. For creating functional maps of human cortex during more complex cognitive tasks, MEG is often combined with fMRT, as the two methods complement each other. Neuronal (MEG) and hemodynamic (fMRT) data may not be in agreement, even though there is a tight relationship between local field potentials (LFP) and blood oxygenation level-dependent (BOLD) signals. MEG and BOLD signals may originate from the same source (though the BOLD signals are filtered through the hemodynamic response) (Source: "Magnetoencephalography," Wikipedia, accessed Aug. 8, 2016).

FIG. 1 illustrates a display system and method for customizing a controller in a display system that includes assessing cognitive brain capacity according to an embodiment of the invention. System 100 includes a display device 102 for displaying information 108, or representations thereof, to a subject 104. The information can be a visual stimulus displayed to evoke a measurable brain activity response, such as the stimulus shown FIG. 11A. Brain activity in the subject's left and right hemispheres 132, 134 can be measured using a detector 130. Suitable detectors are described herein and include devices that measure EEG signals, MEG signals, infrared signals, fMRI BOLD signals, or the like.

The subject's visual space 106, which is schematically illustrated in FIG. 1 as a fan-shaped region, includes a left half (left hemifield) 110 and a right half (right hemifield) 112. Displaying the information can include generating representations of information 108 in a manner accounting for independent cognitive capacities corresponding to the subject's left and right halves 110, 112 of visual space 106.

The display device 102 may include a computer or processor configured to perform the various embodiments or aspects of the invention as described herein, including, but not limited to, generating the representations (e.g., visual stimuli) 108, adjusting the representations, and assessing independent cognitive capacities, for example, by determining at least one metric of the independent cognitive capacities. As shown, the display device 102 can be functionally coupled to a controller 150 and a separate computer or processor 152 configured to perform the various embodiments or aspects of the invention.

In the system 100 of FIG. 1, the controller 152, if present, causes the display device 102 to display the visual stimulus at at least one known location relative to the subject's eye gaze. The display system 100 includes a detector 130 to measure brain activity of the subject's left and right brain hemispheres 132, 134 in response to the subject's viewing of the stimulus. The brain activity has a frequency component associated therewith. The system 100 includes at least one processor 152 coupled to the detector 130 and configured to process the measured brain activity to determine a frequency-dependent metric of the brain activity, assess independent cognitive capacities of the subject's left and right brain hemispheres based on the frequency-dependent metric of the brain activity, and adjust a function of the controller 150 according to the assessment of the independent cognitive capacities.

While the system and method of FIG. 1, and other embodiments described herein, are described with respect to generating and displaying a visual stimulus or other visual representations of information, the embodiments or concepts described herein may be equally applied to other ways of presenting the stimulus or other representations of information, including filtering the stimulus or representations or displaying the stimulus or representations in accordance with one or more tags associated with the information, e.g., in an augmented reality display.

As shown in FIG. 1, the stimulus 108 includes representations (or objects) 114, which are displayed in the left half of the visual space 106, and representations (or objects) 116, which are displayed in the right half of the visual space. Each object may be considered a stimulus. The stimulus 108 may be generated by using a temporal profile associated with the left or right half of the visual space 106 to maintain cognitive capacity performance in connection with the respective half.

The system 100 can include a device, e.g., a gaze monitor 118 including a camera 117, to monitor eye gaze 122 of the subject 104. The eye gaze 122 (illustrated here as a single arrow) may be monitored by tracking eye position with the camera 117. This is typically done to ensure the subject's gaze is centered on the displayed information, e.g., on a fixation point 115, as shown in FIG. 1. The camera 117 may be a separate camera functionally coupled to the display device 102, as shown, or a camera integrated into the display device 102. For illustration purposes, the current field of view 120 of the subject 104 is shown in FIG. 1 to coincide with the visual space 106. Displaying the information can include dividing the current field of view 120 based on the subject's eye gaze 122 as a function of the independent cognitive capacities corresponding to the subject's left and right halves 110, 112 of the visual space 106. The display device 102 may be a computer display, a head-up display (HUD), or a head mounted display (HMD), and can be a virtual reality (VR) or augmented reality (AR) display. The display device (or information being displayed, e.g., the stimulus being displayed) may be adjusted, e.g., shifted, to align with the current field of view 120 based on the monitored eye gaze.

The system and method 100 may include determining at least one metric representative of the independent cognitive capacities. The at least on metric may be determined for an individual subject, e.g., the subject 104, using a behavioral test to measure the subject's independent cognitive capacities. For example, the test can be administered using the display device 102 to display the test (e.g., a series of visual stimuli) to the subject 104 and to elicit a response, e.g., a behavioral response, a measurable physiological response, or both. The subject's response may be captured via an input device, such as a keyboard, touch screen, or microphone, any and all of which may be integrated into display device 102, or via a camera, such as camera 117. An example of a cognitive test using a computer display and a camera to monitor gaze (or eye position) is described in the Example 6 below with reference to FIG. 11A. Alternatively or in addition, the at least one metric representative of the independent cognitive capacities can be determined directly by measuring brain activity and analyzing oscillatory power of brain waves as described herein.

Figure 3:
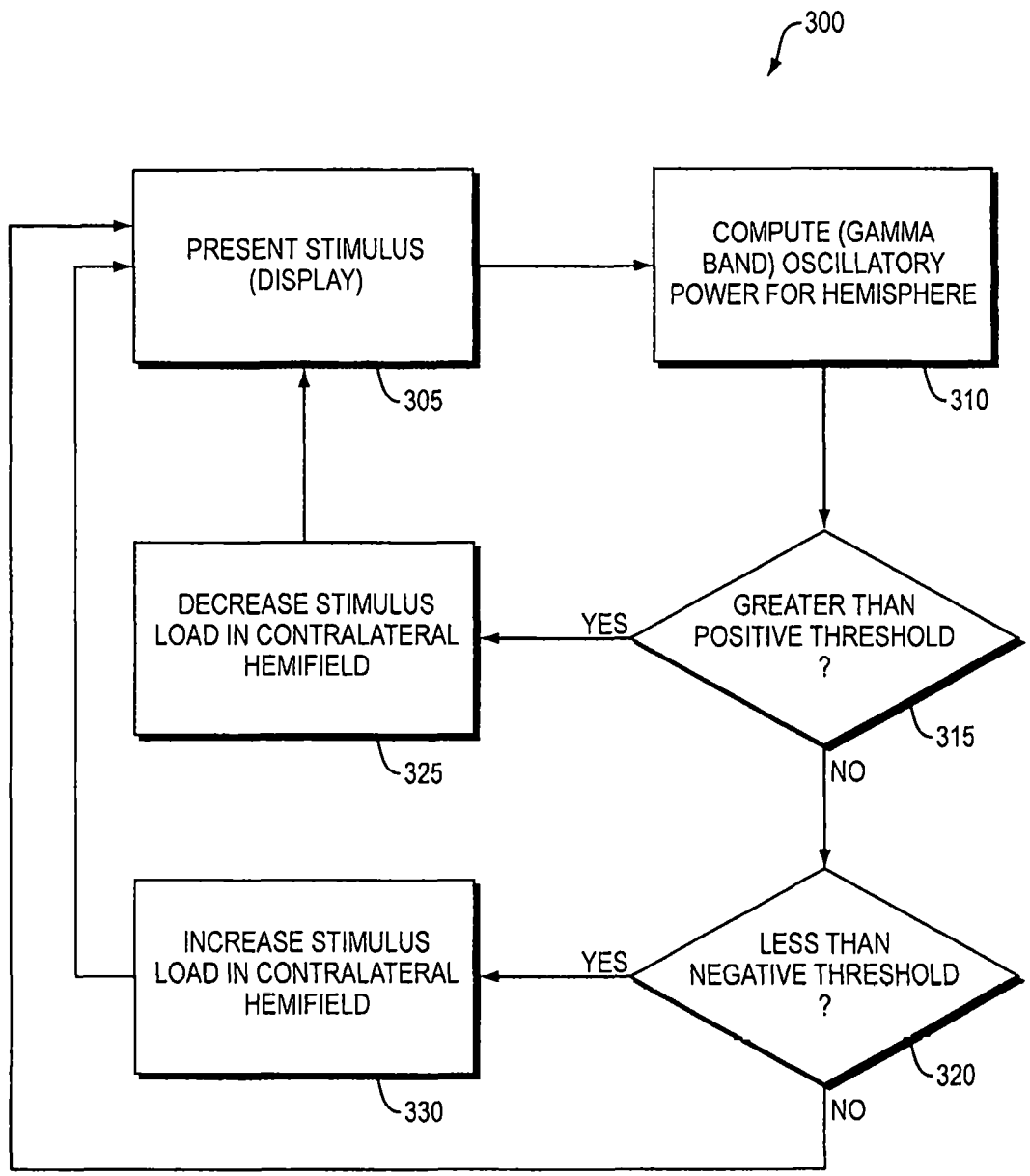
FIG. 3 is a block diagram illustrating a method for adjusting a stimulus being displayed based on measured brain activity.

The displaying of the visual representations (visual stimuli) 108, e.g., on the display device 102, may be adjusted as a function of the at least one metric representative of the independent cognitive capacities. For example, adjusting the visual representations displayed can include adjusting any of number, position, size, color, distribution, density, and symmetry of the visual representations (stimuli) 108 being displayed via the display device 102 as a function of the at least one metric. Adjusting the stimulus being displayed may include reducing or increasing stimulus load, e.g., reducing or increasing the number of representations (stimuli) 108 being displayed, when the metric exceeds or falls below a threshold value. An example process for dynamically adjusting a stimulus being displayed based a measure of frequency-dependent brain activity is schematically illustrated in FIG. 3.

The information displayed need not be stationary but can move within the visual space 106, e.g., from the left half 110 to the right half 112 of the visual space, or from the right half 112 to the left half 110 of the visual space. In the example shown in FIG. 1, movement is schematically shown with respect to representation 114. Representation 114 is presented in overlapping migration in the left half of the visual space 106, as indicated by arrow 124.

Figure 2:
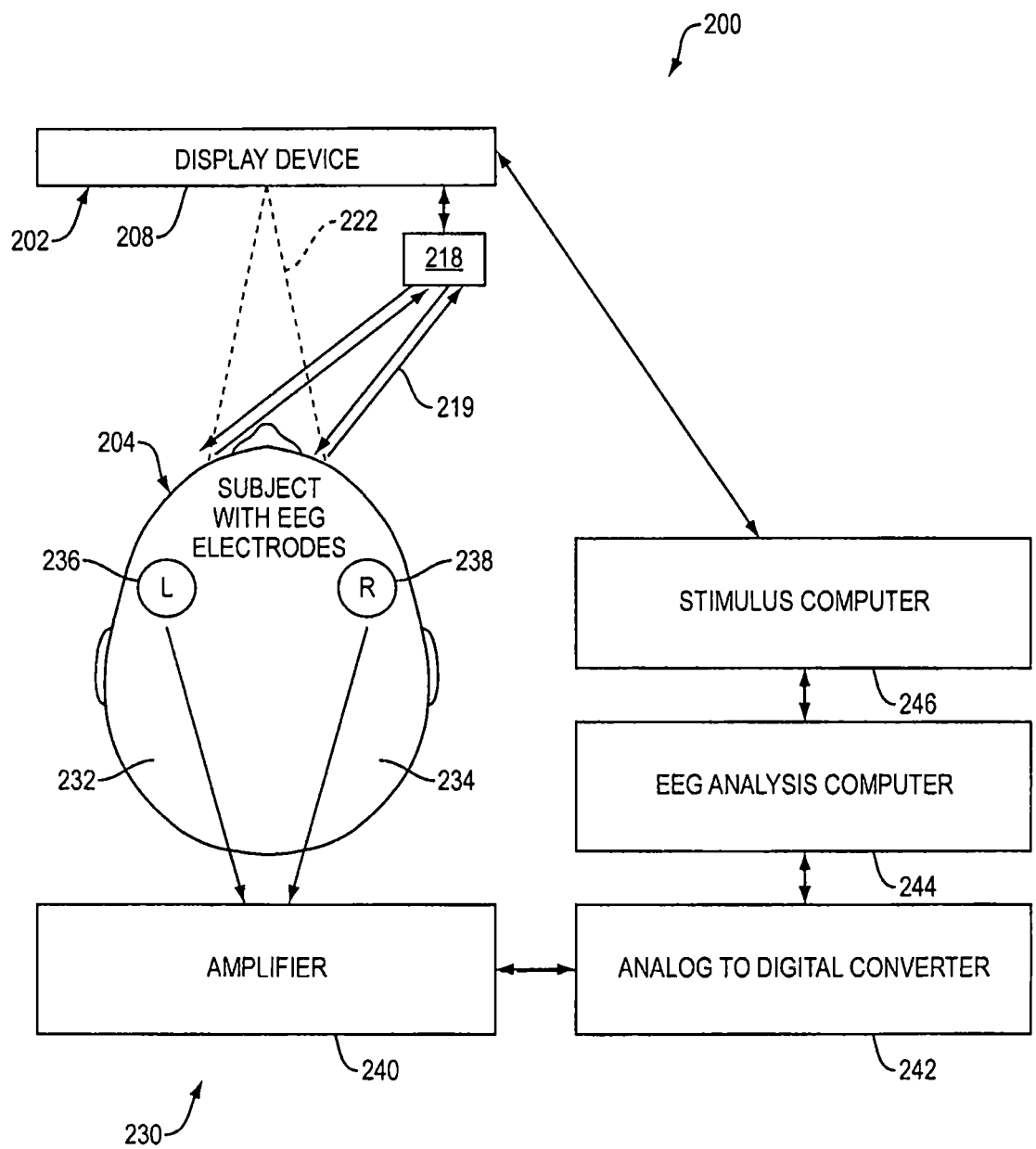
FIG. 2 is a schematic diagram illustrating a display system and method including detecting EEG signals according to an example embodiment.

FIG. 2 illustrates a display system and method according to an example embodiment. The dynamic display system 200 includes a display device 202 to present a stimulus 208 to a subject 204. A detector 230 is provided to measure brain activity of the subject's left and right brain hemispheres 232, 234 in response to the subject's viewing of the stimulus 208. As shown, the detector 230 is an EEG detector that detects EEG signals via electrodes 236, 238 placed on the subject's head over the left and right hemispheres. The EEG detector 230 includes an amplifier 240 and can include or can be coupled to an analog to digital converter (ADC) 242 to process the raw EEG signal detected from the subject's scalp.

As shown in FIG. 2, a first processor 244 (e.g., an EEG Analysis Computer) is coupled to the detector 230 (via ADC 242) and configured to assess independent cognitive capacities of the subject's left and right brain hemispheres based on the measured brain activity. Processor 244 can be configured to compute from the measured brain activity a frequency-dependent metric of the brain activity and assess the independent capacities based on the computed frequency-dependent metric. A second processor 246 (e.g., a Stimulus Computer) is coupled to the first processor 244 and the display device 202. The second processor 246 is configured to adjust a property of the visual stimulus displayed, and/or other visual representations displayed, dynamically according to the assessment of the independent cognitive capacities. To this end, the processor 246 may adjust a function of a controller (e.g., controller 150 in FIG. 1) in the display system. The stimulus being displayed can be adjusted by adjusting a stimulus load in a visual hemifield (e.g., hemifield 110, 112 of FIG. 1) according to the measured brain activity (e.g., the frequency-dependent metric of the brain activity) in the subject's contralateral brain hemisphere. One frequency-dependent metric is oscillatory power, which can be computed over one or more selected frequency bands. The processor 246 can be configured to adjust stimulus load by modulating at least one of the number of objects and the complexity of objects in the stimulus display. The display system can further include a gaze monitor 218, which can be configured to track 219 the subject's eye position to monitor the subject's gaze 222. Gaze monitor 218 can include a camera (e.g., camera 117 of FIG. 1) or other visual sensor to track eye position. For example, gaze monitor 218 can include an infrared camera to image the subject's eyes and can further include an infrared light source to illuminate the subject's eyes, as illustrated by the double-headed arrows 219 in FIG. 2.

The system may be provided with a filter to process (condition) the detected brain activity, such as the signals detected from the EEG electrodes 236, 238 illustrated in FIG. 2. The filter may be implemented as an analog filter. Alternatively, the filter may be implemented as a digital filter. For example, an analog filter may be provided as part of the amplifier 240 or the analog to digital converter 242 illustrated in FIG. 2. Alternatively or in addition, a digital filter may be provided in the EEG analysis computer 244 illustrated in FIG. 2. Any filter design suitable for processing the detected brain activity, such as activity based on EEG signals, may be used. The filter may be selective for one or more frequency bands that have been identified as useful for analyzing brain activity, in particular in the context of assessing independent capacities, as described herein.

FIG. 3 is a block diagram 300 illustrating an example method for adjusting a stimulus being displayed based on brain activity. At 305, a stimulus is presented to a subject while brain activity is being recorded using any of the techniques described herein. At 310, oscillatory power in a selected frequency band, e.g. gamma band, is computed for a hemisphere. Next, the computed oscillatory power is compared to one or more thresholds (315, 320). Based on the result(s) of the comparison, a stimulus load is adjusted (325, 330) in the visual hemifield contralateral to the hemisphere for which the oscillatory power was computed. In the example shown in FIG. 3, if the oscillatory power is greater than a positive threshold (315), the stimulus load is decreased (325) in the contralateral hemifield. Otherwise, the computed oscillatory power is compared (320) to a negative threshold. If the oscillatory power is less than the negative threshold, stimulus load is increased (330) in the contralateral hemifield.

To determine the threshold(s), one can estimate the noise variance (from previous stimuli displayed with identical load conditions) and set the threshold(s) relative to the noise variance or related measure. For example, one can set a threshold at 3-5 standard deviations.

Stimulus load can be adjusted, for example, by changing the number of objects that are displayed or by manipulating object complexity.

Figure 4:
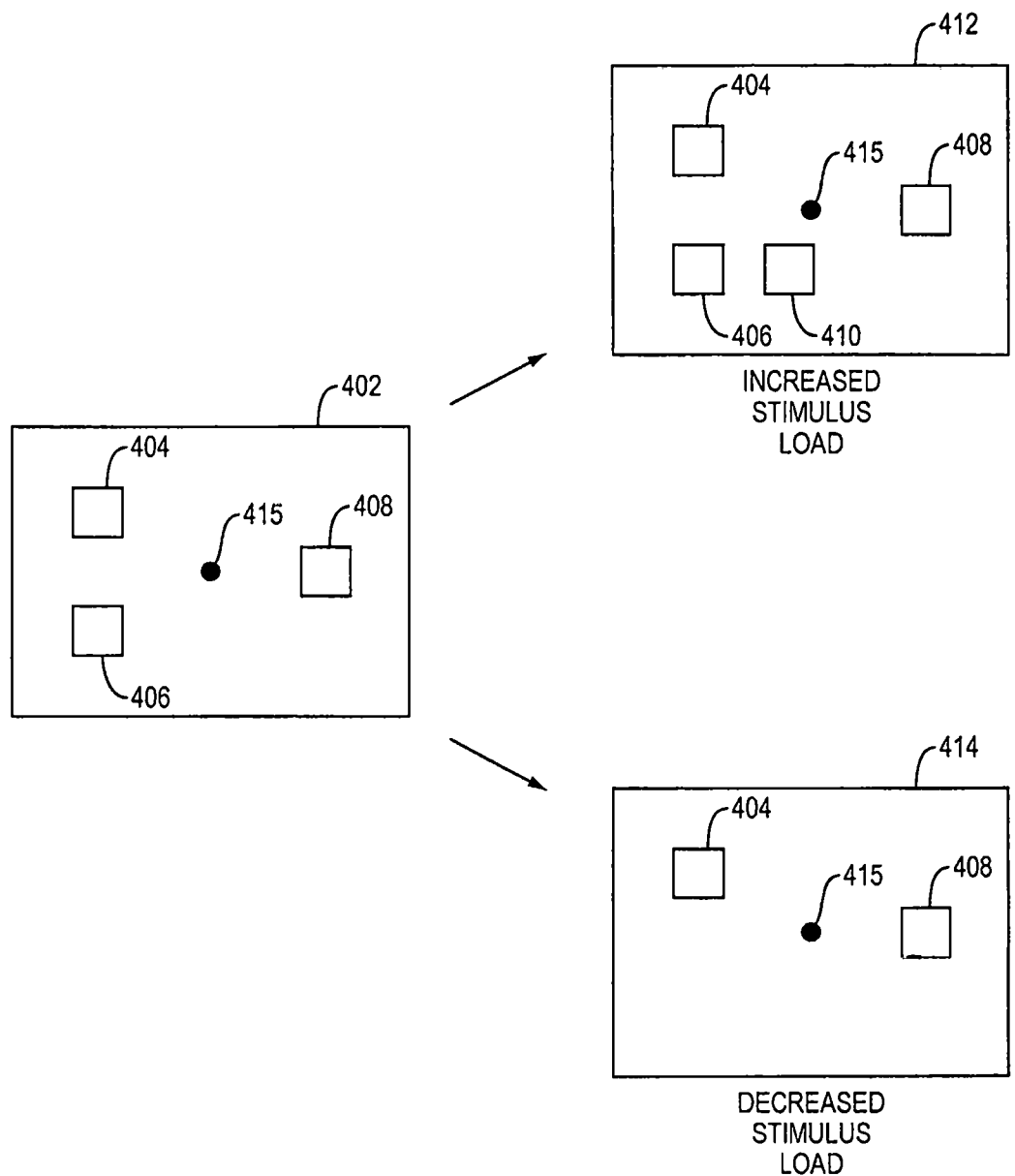
FIG. 4 illustrates adjusting a visual stimulus by adjusting stimulus load in a hemifield.

FIG. 4 illustrates adjusting a property of a visual stimulus being displayed by adjusting stimulus load in a visual hemifield. A property of the stimulus can be a location, size, quantity, color, speed of movement of the stimulus. The concepts illustrated in FIG. 4 can also be applied to other visual representations.

As shown in FIG. 4, visual stimulus 402 includes three objects arranged relative to a (central) fixation point 415. Objects 404, 406 are positioned relative to the fixation point 415 such that the objects are perceived to be in the left visual hemifield of a subject viewing the stimulus 402 when the subject's eye gaze is aligned with (e.g., centered on) fixation point 415 (e.g., the subject is viewing with central gaze). Object 408 is positioned relative to fixation point 415 such that the object is perceived to be in the right visual hemifield of the subject viewing the stimulus 402 being displayed. To increase stimulus load to a hemifield, an additional object may be added to that hemifield. In visual stimulus 412, object 410 is added to objects 404 and 406, to appear in the left visual hemifield, thereby increasing stimulus load to the left visual hemifield. In visual stimulus 414, object 406 of stimulus 402 is removed, thus only object 404 is displayed, thereby decreasing the stimulus load to the left visual hemifield. Note that overall stimulus load (e.g., the combination of stimulus loads of the hemifields) is increased in stimulus 412 relative to stimulus 402 and that overall stimulus load is decreased in stimulus 414 relative to stimulus 402. Instead of increasing the number of objects displayed, by adding object 410 as shown in stimulus 412, stimulus load to the left visual hemifield can be increased by displaying object 408 to the left side of fixation point 415, as opposed to the right side as in stimulus 402. In this way, the stimulus being displayed has a total of three objects, as in stimulus 402, and the overall stimulus load, if measured as total number of objects in both hemifields, would not be changed.

Figure 5:
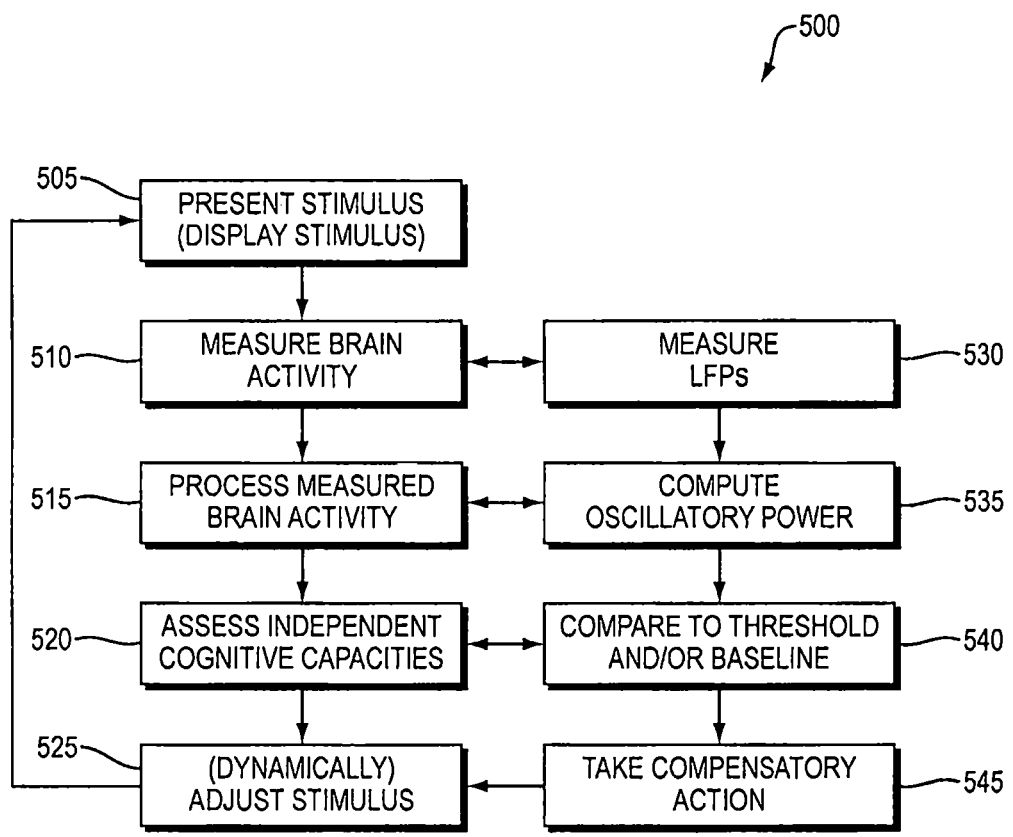
FIG. 5 is a flow diagram of an example embodiment of a method including measuring brain activity and assessing independent cognitive capacities.

FIG. 5 is a flow diagram 500 of an example embodiment of a process for assessing brain activity that can be employed in a method for customizing a controller of a display system or a method for assessing brain injury. At 505, a visual stimulus is presented, e.g., displayed, to a subject. At 510, brain activity is measured using one or more of the techniques and sensors described herein. Brain activity of the subject's left and right brain hemispheres is measured in response to the subject's viewing of the stimulus displayed at 505. Next, at 515, the measured brain activity is processed to generate (e.g., computationally determine) a frequency-dependent metric of the brain activity. At 520, independent cognitive capacities of the subject's left and right brain hemispheres are assessed based on the frequency-dependent metric of the brain activity. As shown at 525, the process can further include adjusting the stimulus displayed (e.g., adjusting a function of a controller in the display system to change a property of the stimulus) according to the assessment of the independent capacities. As described herein (see, e.g., FIGS. 3 and 4 and associated description), adjusting the stimulus displayed can include adjusting a stimulus load in a visual hemifield according to the measured brain activity (e.g., according to a frequency-dependent metric of the brain activity) in the subject's contralateral brain hemisphere. Stimulus load may be adjusted by modulating at least one of the number of objects and the complexity of objects in the stimulus being displayed.

Measuring brain activity (510) can include measuring brain activity with a suitable detector(s) to detect one more of EEG signals, MEG signals, infrared signals recorded from the scalp, BOLD signals from fMRI, and hemodynamic signals from functional ultrasound.

Figure 6:
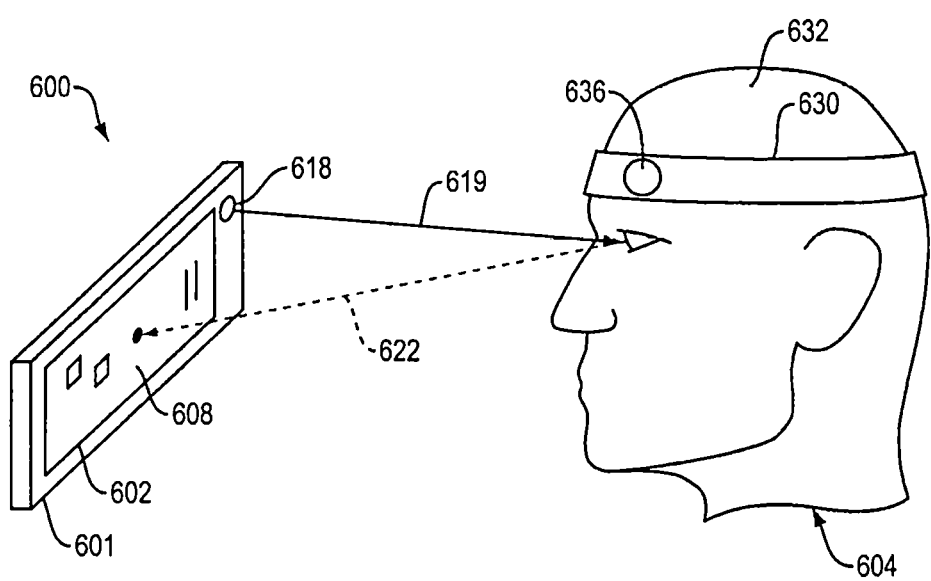
FIG. 6 illustrates an example apparatus or kit including a smart phone device and a wearable sensor device according to an example embodiment.
Figure 10A:
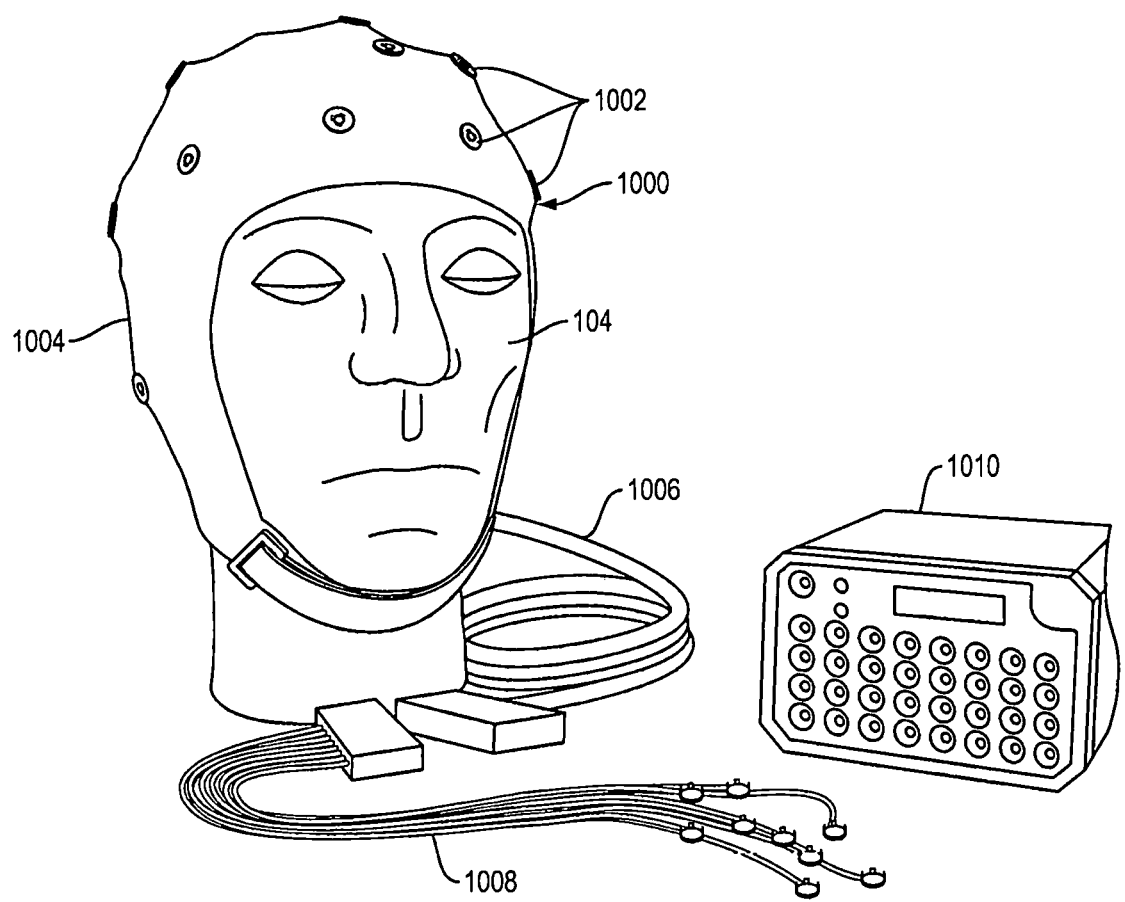
FIGS. 10A and 10B illustrate example wearable devices for measuring EEG signals, which may be used with embodiments of the invention.
Figure 10B:
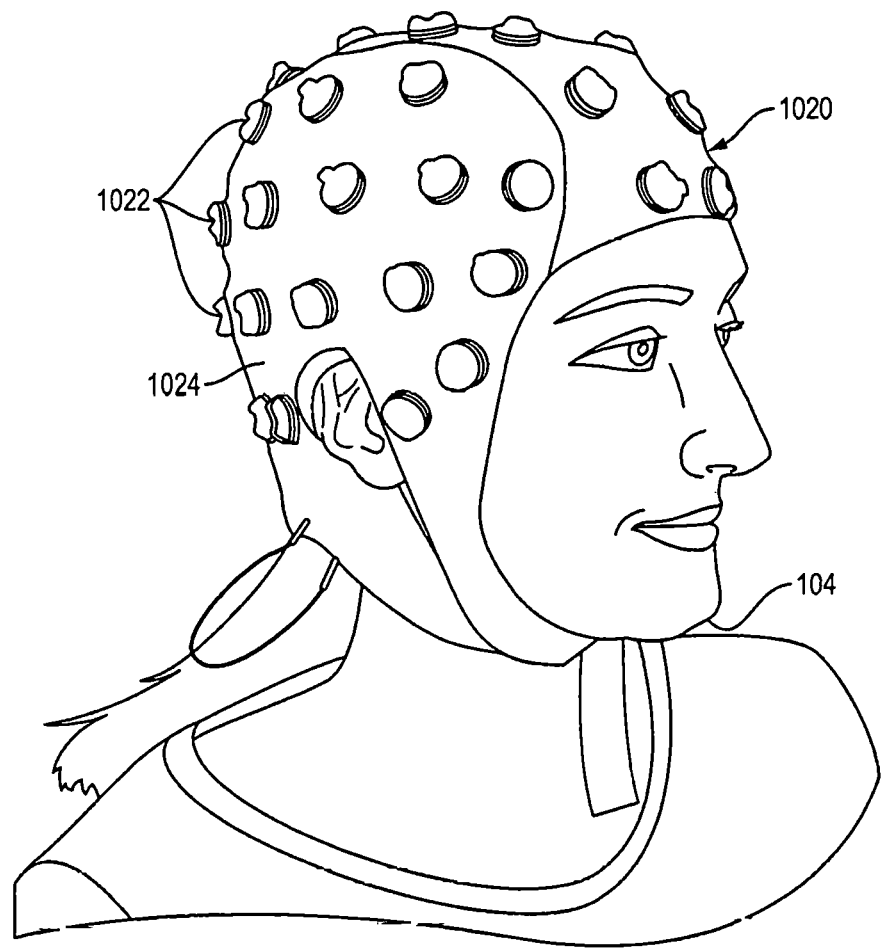

As shown at 530, measuring the brain activity can include measuring local field potentials (LFPs), which can be measured using a wearable EEG detector as described herein (see, e.g., FIGS. 6, 10A, and 10B). As shown at 535, processing the measured brain activity can include computing oscillatory power of the measured local field potentials. The computed oscillatory power can be compared to a threshold value, a baseline value, or both, as shown at 540. At 545, a compensatory action can be taken based on the result(s) of the comparison. For example, the compensatory action can include, for a given brain hemisphere, modulating stimulus load to the contralateral visual hemifield. Stimulus load can be adjusted by adjusting the visual stimulus being displayed (525) or by adjusting other visual representations being displayed.

Brain activity oscillatory power can be computed (535) for one or more selected frequency bands as described herein (see Example 6). The frequency bands can include, for example, a lower frequency band of about 8-50 Hz and a higher (upper) frequency band of about 50 Hz to about 200 Hz, e.g., about 50 Hz to about 100 Hz. For example, gamma band oscillatory power can be analyzed. A ratio of oscillatory power in one frequency band, e.g., the higher frequency band, to oscillatory power in another frequency band, e.g., the lower frequency band, can be computed. Assessment of the independent cognitive capacities can be based on the computed ratio.

The process of FIG. 5 can be used to assess the subject's current level of cognitive function by determining overall capacity of the subject as a function of the independent cognitive capacities. Assessing the subject's current level of cognitive function can include comparing the determined overall capacity to a baseline capacity. The baseline capacity can be an overall capacity or an average of overall capacities previously determined for the subject, or another reference capacity.

Details of the computational methods and example results of the analysis of changes in spectral power of various regions of the brain are described in Example 6 below.

Figure 11A:
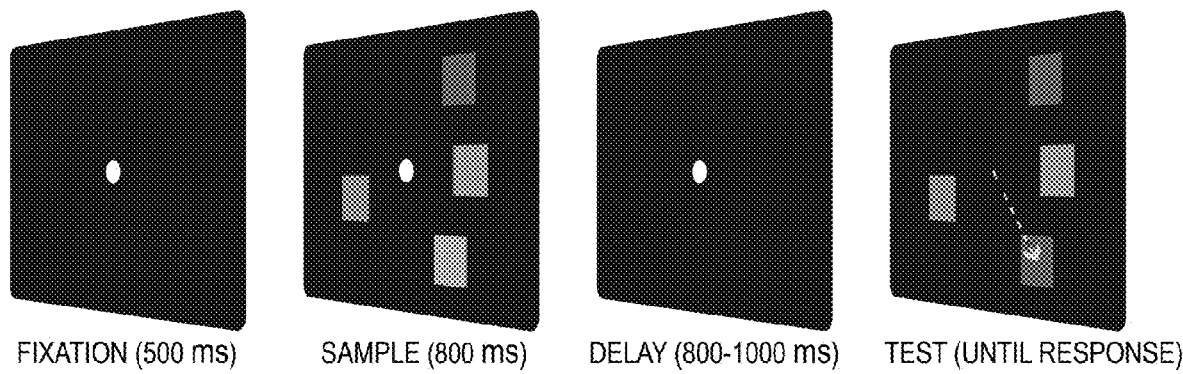
FIG. 11A illustrates a change localization task for use with example embodiments of the invention. After fixating (e.g., directing eye gaze on a fixation point, illustrated by a white circle) for 500 ms, subjects were presented with an array of colored squares for 800 ms. These squares then disappeared, and subjects were required to maintain the colors of these squares in memory for a variable delay of 800-1000 ms. The array then reappeared with a change to the color of one square. The subjects were rewarded for saccading (e.g., moving the eye gaze, illustrated by a dashed arrow) to the changed square.
Figure 12A:
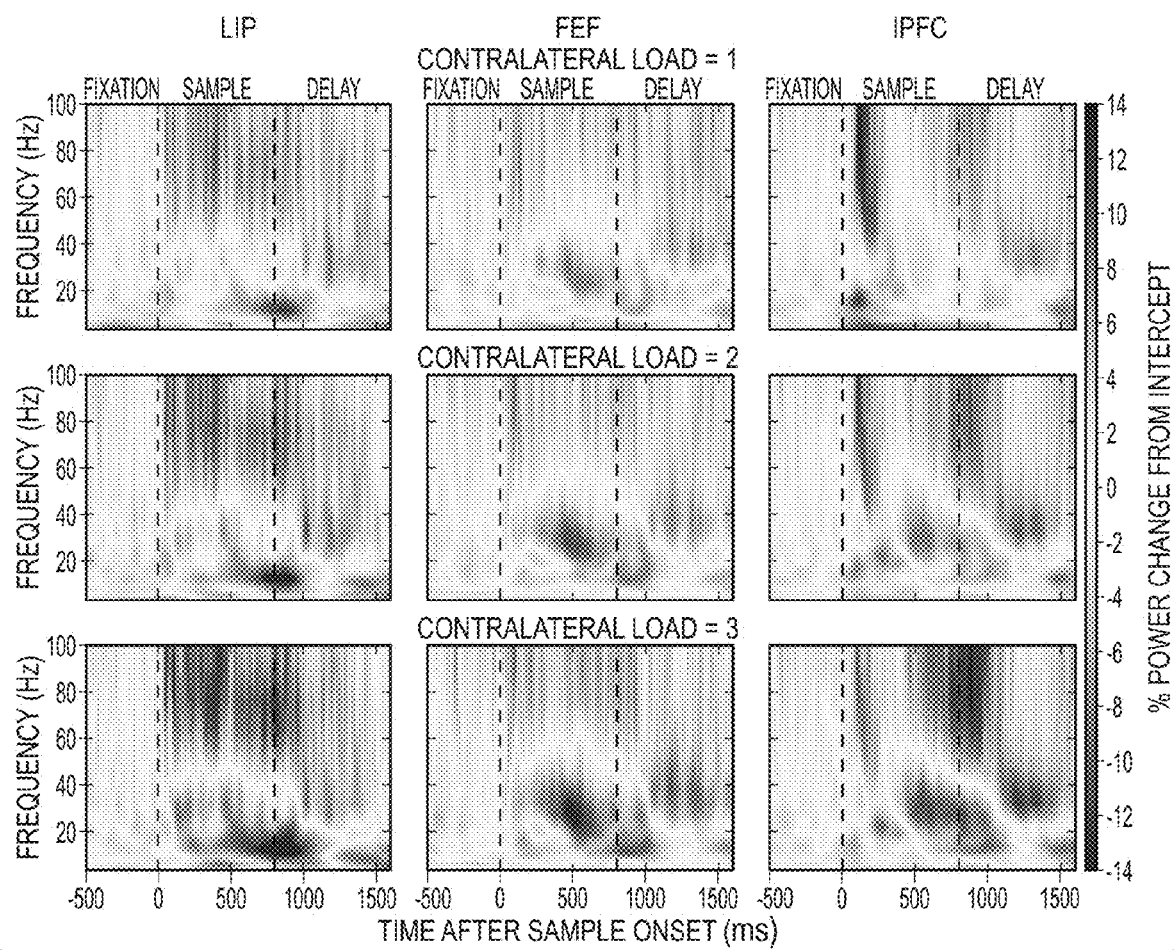
FIGS. 12A-12B show results of the analysis of brain activity.
Figure 12B:
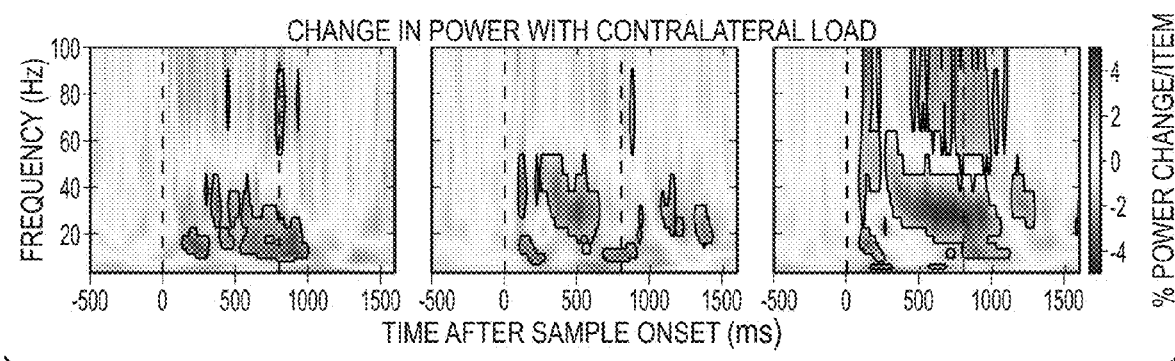
Figure 13A:
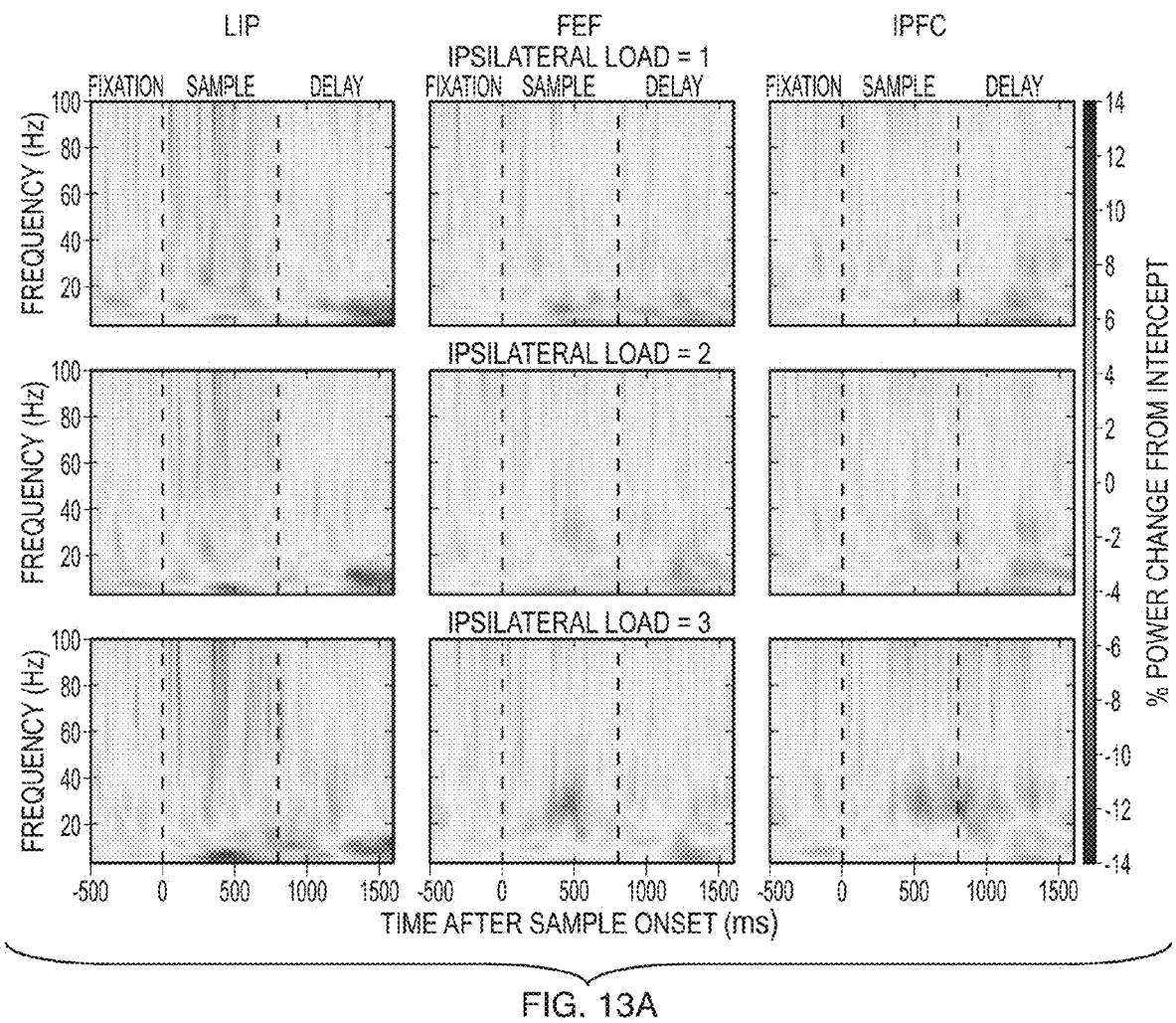
FIGS. 13A-13B illustrate further results of the analysis of brain activity.
Figure 13B:
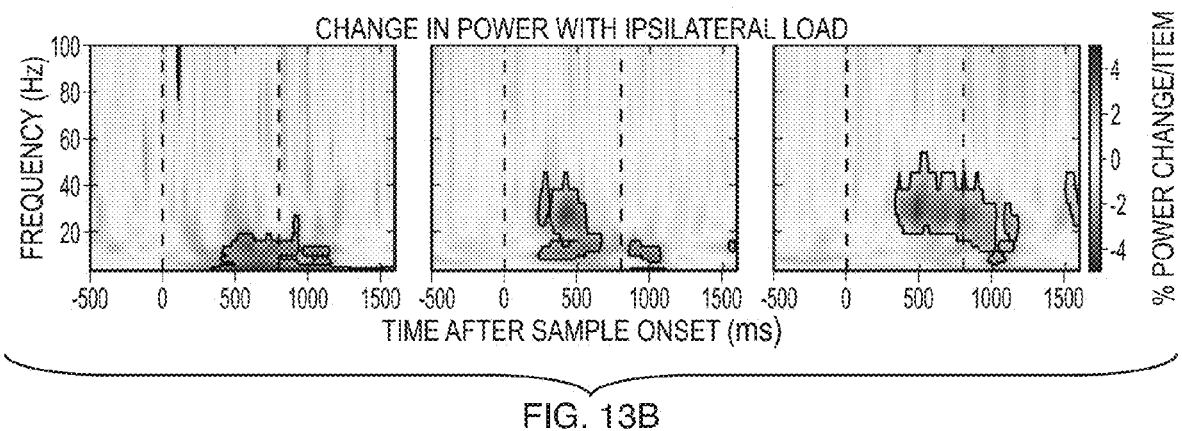

For example, FIG. 12A illustrates percent change in oscillatory power for each contralateral load condition (n=1, 2, 3 objects) across frequency and time computed for local field potentials (LFPs) from the lateral intraparietal cortex (LIP), the frontal eye fields (FEF), and the lateral prefrontal cortex (lPFC). FIG. 12B illustrates percent power change per contralateral load. Similarly, FIGS. 13A-13B illustrate percent power change for ipsilateral loads (n=1, 2, 3 objects) and percent power change per ipsilateral stimulus, respectively. The data shown in FIGS. 12A-12B and 13A-13B were obtained from brain activity recordings in two monkeys performing the behavioral task of FIG. 11A. The data suggest that the prefrontal cortex region shows a larger effect on oscillatory power. Thus, embodiments may focus on measuring brain activity from one or more prefrontal cortex regions to assess independent capacities of a subject. This can simplify the design of the system by reducing the number of detection points (e.g., number of EEG electrodes) and can also reduce the computational demand on a processor in a display system that adjusts the display according to measured brain activity.

Embodiments may include a virtual reality (VR) display configured to present a visual stimulus and/or other visual representations to a subject. A virtual reality display can be wearable and may allow for more accurate assessment of the subject's brain capacity.

An embodiment may be an integrated, system that includes a display device, a processor, and a brain activity detector integrated into a helmet or other wearable device (see, e.g., Example 3). The system as a whole can be wearable and may communicate, e.g., wirelessly, with one or more additional processors (see, e.g., Examples 3 and 4). Such an embodiment may be particularly useful for sports, aviation, law enforcement, and military applications.

Embodiments of the present invention can be implemented in hardware, firmware, or software. If implemented in software, the software can be any language capable of performing embodiments or aspects of the invention described herein. The software can be stored on any form of non-transitory computer-readable media and loaded and executed by an application-specific or general-purpose processor, also capable of performing embodiments of the invention described herein.

EXEMPLIFICATION

Example 1—Smart Phone Device

FIG. 6 illustrates an example system or kit 600 including a mobile device, e.g., smart phone, 601 and a wearable detector 630 according to an example embodiment. The smart phone device 601 includes a display device 602, e.g., a touch screen display, to display a visual stimulus 608. A built-in camera 618 can acquire images (e.g., video images) 619 of the subject 604, which can be used to identify the position and orientation of the subject's eyes to monitor eye gaze 622 of the subject. The detector 630, which is illustrated as a head mounted device, can include one or more sensors 636 to measure brain activity of the subject's left and right hemispheres 632. The detector 630 and mobile device 601 can each include a wireless communication interface to communicate, such as via Bluetooth, WiFi, or other wireless communication protocol. Each of the detector 630 and mobile device 601 can in turn communicate wirelessly with a base station (not shown). The base station can include a database or be configured to access a database.

Example 2—Head-Up Display

Figure 7:
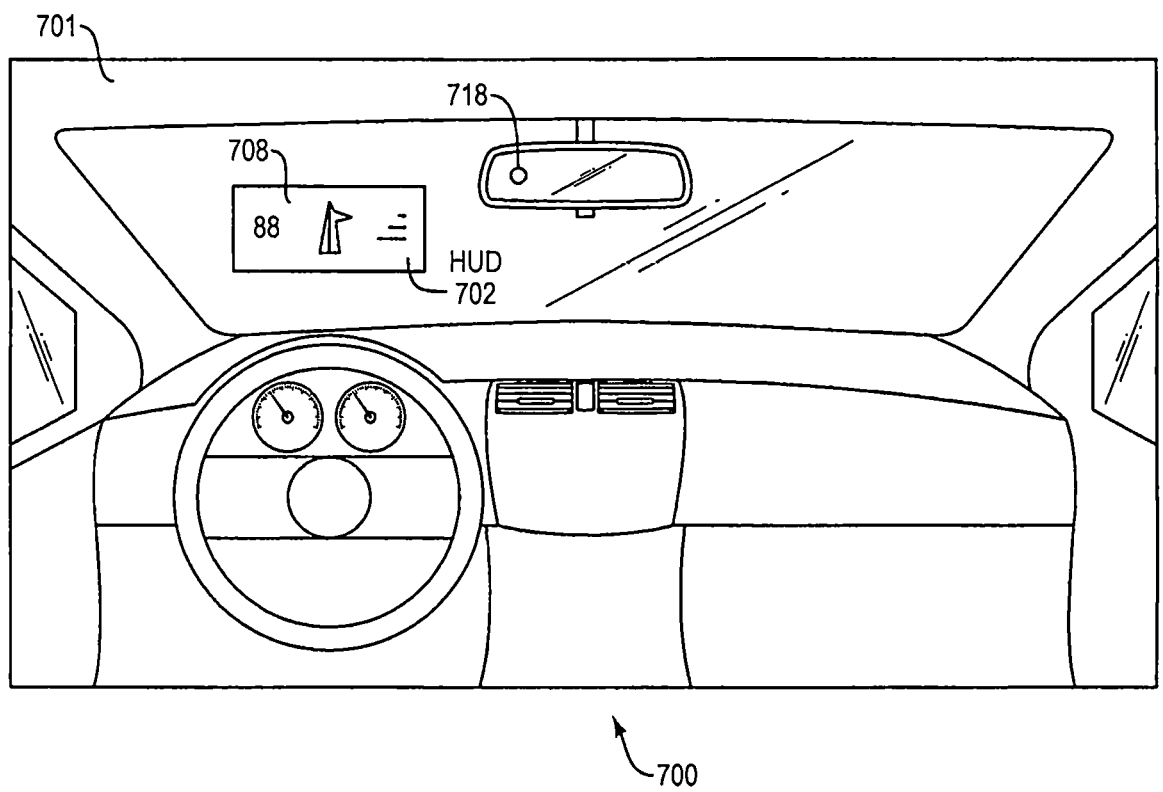
FIG. 7 illustrates a vehicle head-up display (HUD) according to an example embodiment.

FIG. 7 illustrates a display system 700 employed in a vehicle 701 according to an example embodiment. The system includes a head-up display (HUD) 702 to display information, such as a visual stimulus 708 or other visual representations. The vehicle 701 can be a passenger vehicle, a truck, a racecar, or other vehicle where monitoring of the driver's cognitive capacity may be desired. A driver (not shown) can wear a brain activity detector, such as detector 630 shown in FIG. 6 or EEG sensor caps 1000, 1020 illustrated in FIGS. 10A and 10B. A gaze monitor 718, which can be embedded in the rear view mirror as shown, is configured to monitor the driver's eye gaze. The system 700 can use the brain activity measured from the driver to adjust the information being displayed by the HUD 702. The system can use the measured brain activity and information about the monitored eye gaze to assess current level of cognitive function of the driver and, as a result of the assessment, take a corrective action such as, for example, alerting the driver, changing the information displayed to the driver, or adjusting a function of vehicle 701.

Example 3—Helmet Device

Figure 8:
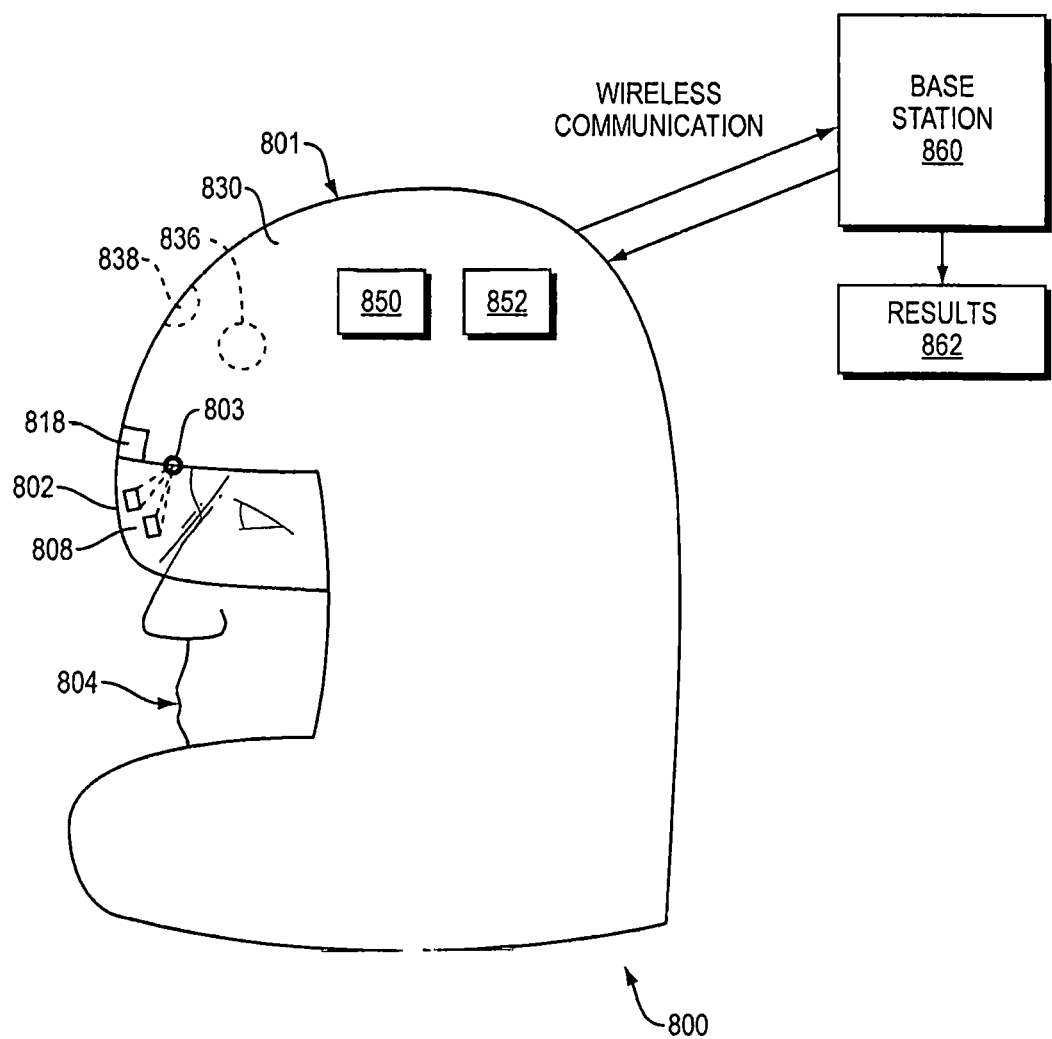
FIG. 8 illustrates a football-style helmet device including a display and brain activity sensor(s) according to an example embodiment.

FIG. 8 illustrates a system 800 for assessing a concussion or other brain injury. The system includes a football-style helmet device 801 with integrated display device 802 and brain activity detector 830. The display device 802 can display one or more stimuli 808 to subject 804 wearing the helmet device 801. As illustrated, the display device 802 can include a projector 803 to project an image onto a visor of the helmet device, thereby displaying a stimulus 808 to the subject 804. A gaze monitor 818 can be included in the helmet device to monitor the subject's eye gaze while the subject is viewing the stimulus 808 displayed. The detector 830 can include one or more sensors 836, 838 to detect brain activity of the subject's left and right hemispheres. The sensors 836, 838 can be EEG electrodes embedded in the helmet device 801. The helmet device can further include a controller 850 in communication with the display device 802 and a processor 852 in communication with the controller and the detector 830. The controller 850 causes the display device 802 to display the visual stimulus 808 and/or other visual representations. The processor 852 is configured to receive brain activity signal from the detector 830 and process the signals received, e.g., by filtering the signals. The controller 850, the processor 852, or both can be configured to communicate wirelessly with a base station 860. The base station can receive data relating to the brain activity measurements from the device 801, process the measured brain activity data to determine a frequency-dependent metric of brain activity, and assess independent cognitive capacities of the subject's brain hemispheres. The base station 860 can output a result 862, which can include an indication of brain injury as a function of the assessment of the independent cognitive capacities. The base station may also send the result to the device 801 for display to the subject 804.

Example 4—Cloud-Based Server

Figure 9:
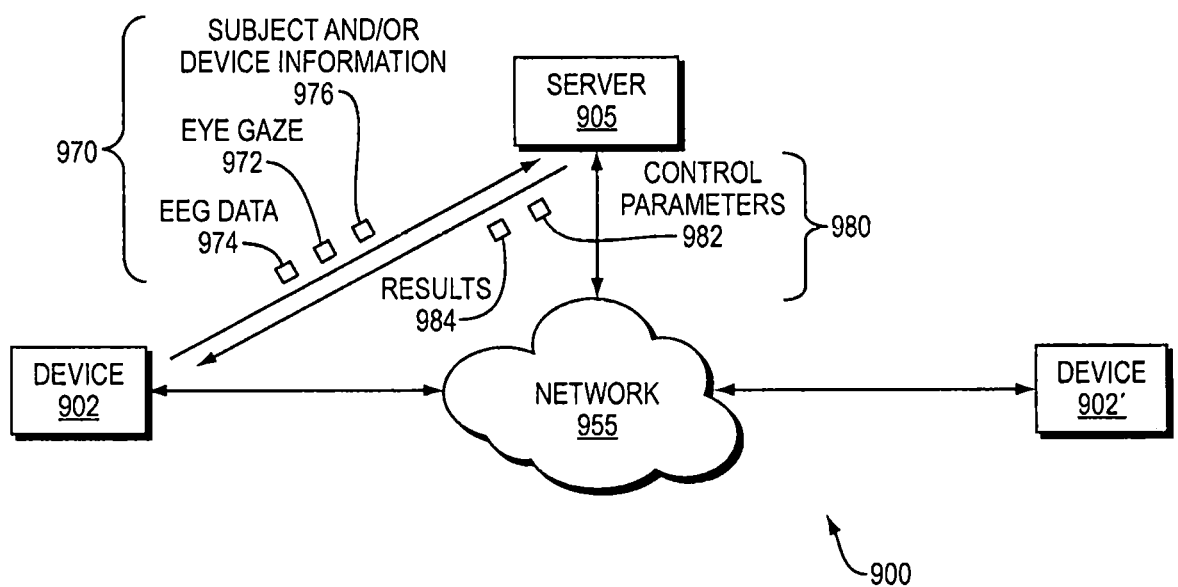
FIG. 9 illustrates an example cloud-based network in which embodiments of the invention can be deployed.

FIG. 9 illustrates an example cloud-based network 900 in which embodiments of the invention can be deployed. Devices 902, 902' communicate with server 905 through cloud network 955. Each device 902, 902' can be any of the display systems and devices described herein, such as systems or devices 100, 200, 600, 700, 800. As illustrated for device 902, the connected devices can send eye gaze information 972, and brain activity information 974 (e.g., EEG data), and other device and/or subject information 976, collectively referred to as client device data 970, to the server via network 955. The server processes the data received and sends server data 980, which can include control parameters 982 and results 984. Server data 980 may be sent in response to client data 970 received from any one of devices 902, 902'.

Example 5—EEG Head Caps

FIGS. 10A and 10B illustrate example head-worn devices for measuring EEG signals from brain hemispheres that may be used with embodiments of the present invention. FIG. 10A shows a NEXUS EEG cap 1000, which is an EEG electrode device with plural (e.g., 21) electrodes 1002 built into a stretchable cap 1004 (Mind Media B.V., Herten, The Netherlands). Device 1000 is shown with the stretchable cap 1004 positioned on subject's 104 head. Also shown are cable 1006 and connector 1008 to connect the device to a signal conditioner 1010.

FIG. 10B shows a WAVEGUARD TOUCH™ device 1020, which includes an EEG head cap 1024 with plural (e.g., 8 or 64) dry touch-electrode sensors 1022 (ANT Neuro, Enschede, The Netherlands). Device 1020 is shown on subject 104.

Example 6—Stimulus Load and Oscillatory Activity in Higher Cortex

Exploring and exploiting a rich visual environment requires perceiving, attending, and remembering multiple objects simultaneously. Recent studies have suggested that this mental "juggling" of multiple objects may depend on oscillatory neural dynamics. Local field potentials were recorded from the lateral intraparietal area, frontal eye fields, and lateral prefrontal cortex while monkeys maintained variable numbers of visual stimuli in working memory. The monkey's behavior suggested independent processing of stimuli in each hemifield. During stimulus presentation, higher frequency power (50-100 Hz) increased with the number of stimuli (load) in the contralateral hemifield, while lower frequency power (8-50 Hz) decreased with the total number of stimuli in both hemifields. During the memory delay, low frequency power increased with contralateral load. Load effects on higher frequencies during stimulus encoding and lower frequencies during the memory delay were stronger when neural activity also signaled the location of the stimuli. Like power, higher frequency synchrony increased with load, but beta synchrony (16-30 Hz) showed the opposite effect, increasing when power decreased (stimulus presentation) and decreasing when power increased (memory delay). Results suggest roles for lower frequency oscillations in top-down processing and higher frequency oscillations in bottom-up processing.

While a wealth of studies have investigated how humans and animals remember single objects, less is known about how humans and animals remember multiple objects simultaneously. It is well-known that human capacity for multiple items is severely limited: The average adult human can only hold 3-4 objects in mind (working memory) simultaneously (Luck and Vogel 1997; Vogel et al. 2001). fMRI signals from a variety of brain areas are modulated by the number of remembered stimuli (stimulus load) (Linden et al. 2003; Todd and Marois 2004). Similarly, EEG event-related potentials scale with stimulus load, saturate when behavioral capacity is exceeded, and reflect individual differences in working memory capacity (Vogel and Machizawa 2004; Vogel et al. 2005; McCollough et al. 2007; Ikkai et al. 2010; Luria and Vogel 2011). However, multiple-item working memory processes are much less studied in animals, where one can assess neural activity with greater temporal and spatial precision.

Correlates of multiple-item working memory in individual neurons in frontal and parietal cortex were previously reported (Buschman et al. 2011). Monkeys performed a human test of capacity (FIG. 11). Two arrays of 2-5 colored squares were separated by a memory delay. The color of a random square was changed. Monkeys were trained to saccade to this change. Multiple electrodes were implanted in lateral prefrontal cortex (lPFC), frontal eye fields (FEF), and lateral intraparietal area (LIP). These regions are critical for short-term memory (Passingham 1975; Kowalska et al. 1991; Sawaguchi and Goldman-Rakic 1991; Li et al. 1999) and human studies implicate them in capacity limitations (Linden et al. 2003; Todd and Marois 2004, 2005; Vogel and Machizawa 2004; Palva et al. 2010; Voytek and Knight 2010). On the neuron level, capacity limitations were found to be bottom-up (appearing in parietal before frontal cortex), neural information about the target stimulus decreased with stimulus load even when these stimuli was correctly remembered, and neural information was present but reduced in trials in which the animal failed to select the correct target (Buschman et al. 2011).

Here, these data are used to examine effects of stimulus load on oscillations of local field potentials (LFPs). There is increasing evidence that oscillations play a role in cognition. Different oscillatory frequencies may mediate feedforward versus feedback processing (Engel et al. 2001; Buschman and Miller 2007; Engel and Fries 2010; Arnal and Giraud 2012; Bastos et al. 2015) and dynamically link neurons into ensembles (Gray et al. 1989; Buschman et al. 2012; Salazar et al. 2012). Capacity limits have been hypothesized to arise from coding of different stimuli at different oscillatory phases (Lisman and Idiart 1995; Siegel et al. 2008; Lundqvist et al. 2011). The few human EEG studies investigating oscillatory activity showed that power and synchrony increases with stimulus load across a range of frequencies (Jensen and Tesche 2002; Howard et al. 2003; Meltzer et al.

2008; Palva et al. 2010, 2011). But the link between oscillations and multiple item working memory is not well-studied and thus far from understood.

Materials and Methods

Behavioral Task

One adult male rhesus macaque (*Macaca mulatta*) and one adult male cynomolgus macaque (*Macaca fascicularis*) were trained to perform a change localization task. All procedures followed the guidelines of the Massachusetts Institute of Technology Committee on Animal Care and the National Institutes of Health. Animals fixated for 500 ms to initiate a trial. After this fixation period, an array of 2-5 colored squares (1-3 per hemifield) appeared for 800 ms. The stimuli then disappeared. After a 800-1000 ms memory delay period, the array reappeared with a change to the color of a random square. The animal received a juice reward for making a direct saccade to the changed square. From the start of the trial until the presentation of the second array of colored squares, the animal was required to fixate within 1.75 degrees of a central fixation point.

The location of the target was randomized for each trial. However, in order to permit inspection of neural encoding of visual information during the delay period, square locations were chosen from 6 positions (3 per hemifield) in any single session, and only 2 colors could be present at any single position. Additionally, given behavioral evidence for the independence of working memory representations in each hemifield, in each trial, the number of stimuli in each hemifield was manipulated rather than the total number of stimuli in the display, while constraining the total number of stimuli to between two and five. In order to maintain behavioral performance and to acquire a sufficient number of trials with low total load, trials with fewer stimuli in a given hemifield were presented at higher probability than trials with greater numbers of stimuli. This trial selection procedure was uninformative about the location of the target and did not provide any additional information that could assist in the performance of any given trial.

New stimulus locations and colors were randomly selected before each recording session. Stimulus locations were selected to be within 75 degrees of polar angle from the horizontal meridian and between 4-6 degrees of visual angle from the central fixation point, and colors were manually inspected to ensure sufficient discriminability. All twelve possible colors in a given session were unique. An infrared video eye tracking system (ISCAN) recorded eye positions at 240 Hz. A computer running the MonkeyLogic software (Asaad and Eskandar 2008) controlled the stimulus display and behavioral reward.

Electrophysiological Recording

Epoxy-coated dura-piercing tungsten electrodes (FHC) were lowered into each region using a custom-built grid and microdrive assembly that lowered electrodes in pairs using a single screw. Recordings were performed using a Plexon Multichannel Acquisition Processor. All signals were referenced to ground. Local field potentials (LFPs) were filtered with hardware filters between 3.3 Hz and 88 Hz prior to amplification and sampled at 1000 Hz. 2-pole notch filters at 60 Hz (line noise frequency), 85 Hz (monitor refresh rate), and 120 Hz (line noise harmonic) were applied prior to data analysis.

Analyses were restricted to electrodes from which at least one single unit was recorded. Only parietal electrodes whose units showed a spatially selective response in this task ($p<0.05$, permutation test of $\omega^2$) were included in further analyses. Electrodes in FEF and lPFC were differentiated using microstimulation. Out of 1125 recorded electrodes, 546 electrodes fit the selection criteria (13-28 per session, mean 19.5, inter-quartile range 18-21.25). Of these channels, 142 were in LIP (1-9 per session, mean 5.1, inter-quartile range 3.75-7.25), 155 were in FEF (1-12 per session, mean 5.5, inter-quartile range 4.75-6), and 249 were in lPFC (5-15 per session, mean 8.9, inter-quartile range 7-10.25).

Estimation of Behavioral Capacity

The procedure for estimating behavioral capacity by mutual information is described in detail in Buschman et al. (2011). To determine mutual information for the entire display, for each load, the procedure includes computing the conditional mutual information between the animal's choice and the target given the stimulus display. The procedure further includes dissociating the amount of mutual information in each hemifield using linear regression. Full details are provided in the Supplementary Methods, including the Supplementary Figures S1-S4, of Kornblith et al. (2016), which are incorporated herein by reference it their entirety and which are available online at cercor.oxfordjournals.org.

Data Analysis

All analyses were performed using the Julia programming language (julialang.org). Evoked potentials were removed prior to analysis. Spectrograms and coherograms in FIGS. 12, 13, and 16, and Supplementary Figure S2 were computed by continuous wavelet transform with Morlet wavelets. Bar and line graphs in FIGS. 14-17 and 19, and Supplementary Figures S1, S3, and S4 were computed using multitaper time-frequency transforms. Confidence intervals and significance tests were computed using parametric bootstrapping (see Supplementary Methods).

Spectral power was fit using a generalized linear model with a Gamma likelihood function and a logarithmic link function, which yielded a better fit to the data than an ordinary least squares fit. To assess information present in power, adjusted $R^2$ was computed for the gamma model fit, as described in Mittlböck and Heinzl (2002). Further details are provided in the Supplementary Methods.

To determine the relationship between synchrony and load (FIGS. 18, 19, and Supplementary Figures S2 and S3), for each electrodes pair, time point, and frequency, surrogate coherence values were computed with each individual trial removed, yielding an estimate of the contribution of that trial to coherence (Womelsdorf et al. 2006; Hipp et al. 2011; Richter et al. 2015). Then, the correlation between these surrogates and load was computed (see Supplementary Methods). To compute synchrony statistics for individual load conditions, the pairwise phase consistency was used (Supplementary Figure S4), an estimator of the squared mean resultant length that is not biased by the number of trials (Vinck et al. 2010).

Results

Monkeys Maintain Multiple Items in Working Memory

The change localization task and behavioral results are described in detail in Buschman et al. (2011). Animals saw a sample array of 2 to 5 colored squares for 800 ms (FIG. 11A). After an 800-1000 ms delay period, the array reappeared with a change to the color of one of the squares. Animals had to saccade to the changed square to receive a juice reward. The "target" was defined as the stimulus that changed between the two array presentations. The monkey was not cued to (and could not predict) which stimulus would be the target.

Figure 11B:
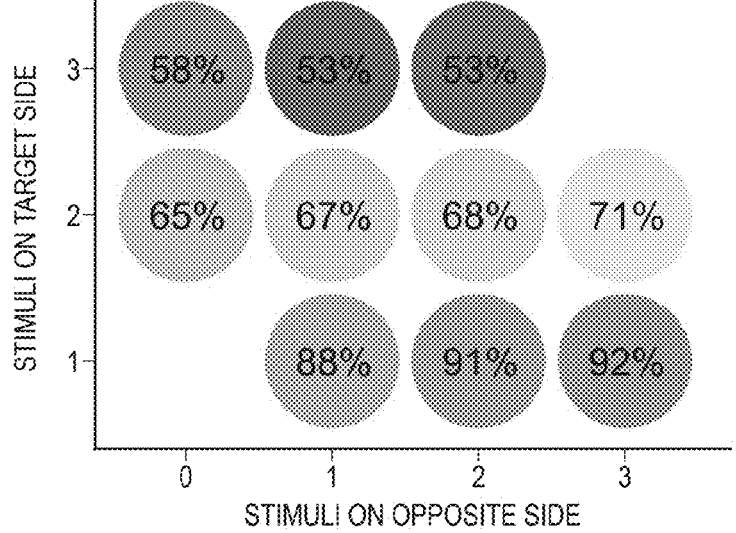
FIG. 11B illustrates average behavioral performance according to the number of squares (stimuli) on the same side as the changed stimulus ("target side") and the number of squares (stimuli) on the opposite side. Performance depended on the number of squares on the target side, not the total number of squares.
Figure 11C:
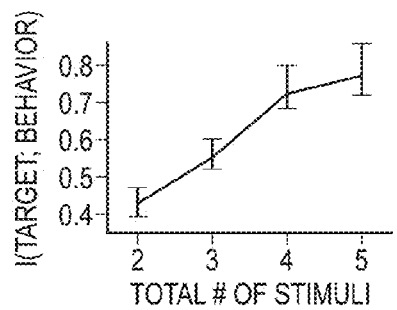
FIG. 11C is a graph illustrating mutual information between the location of the target stimulus and the subject's choice given the display for total loads (e.g., total number of stimuli) 2 through 5.
Figure 11D:
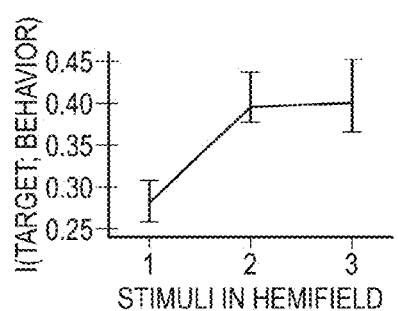
FIG. 11D is a graph illustrating mutual information between the location of the target stimulus and the animal's choice given the display for loads 1, 2, and 3 in the target hemifield. Error bars reflect 95% confidence intervals based on non-parametric bootstrapping across sessions.

As Buschman et al. (2011) reported and others have confirmed (Matsushima and Tanaka 2014), the right and left visual hemifields seemed to process stimuli separately. There were independent capacities on the right and left for the number of stimuli that could be processed/remembered: A stimulus in the same hemifield as the target degraded both the ability of the animal to detect its change and the neural information present about that stimulus. By contrast, a stimulus in the opposite hemifield had little or no effect. Indeed, task performance showed a strong dependence on the number of stimuli in the same hemifield as the target ($p<10^{-10}$, ANOVA; FIG. 11B) but no significant dependence on the number of stimuli in the opposite hemifield from the target ($p=0.23$, ANOVA). To determine the animal's behavioral capacity, mutual information between the animals' choices and the target position were measured (FIG. 11C). Mutual information between the target and response plateaued at 4 items in the display, consistent with reports of working memory capacity of 3 to 4 items in humans (Luck and Vogel 1997; Vogel et al. 2001). Because the behavioral analysis above suggested that the hemifields had independent working memory capacities, linear regression was used to separate information in each hemifield (see Materials and Methods). Information increased when a second stimulus was added to the target hemifield ($p<10^{15}$, bootstrap Z-test; FIG. 11D), but showed no change when a third stimulus was added ($p=0.94$). Thus, behavioral capacity appears to saturate between 1 to 2 stimuli per hemifield.

Oscillatory Power Correlates with Contralateral and Ipsilateral Stimulus Load

The effects of contralateral stimulus load on LFP power were tested using a generalized linear model. After removing evoked potentials, the instantaneous power at each frequency band and each time point in the trial was regressed (see Materials and Methods). The multiplicative contribution over the model intercept was estimated, which estimates the power in the absence of any stimuli. FIG. 12 (Panel A) shows the percent power change for each contralateral stimulus load condition. FIG. 12 (Panel B) plots the percent change in LFP power for each added contralateral stimulus, as estimated based on observed power at loads one to three. The black polygons indicate time-frequency "zones" of significant changes in power with increasing load (see Materials and Methods). FIG. 13 shows the same analysis for ipsilateral stimulus loads. First, the effects of contralateral loads are considered. Effects of contralateral load can be seen in two broad bands, 8-50 Hz ("lower frequencies", including theta, alpha, beta, and lower gamma) and 50-100 Hz ("higher frequencies" or high gamma). Next, the main effects are summarized. Then, details such as temporal dynamics of the effects are presented.

During sample array presentation, higher frequency LFP power increased with increased contralateral stimulus load (positive correlations, warm colors) while lower frequency LFP power decreased with increased contralateral stimulus load (negative correlations, cool colors). During the memory delay (especially late in the delay), there was no effect of contralateral load on higher frequencies and the effects at lower frequencies inverted (FIG. 12).

FIG. 13 shows the effect of ipsilateral stimulus load on LFP power. Like contralateral load, ipsilateral load inversely correlated with lower frequency LFP power during stimulus presentation. But in contrast to contralateral load, effects of ipsilateral load at higher frequencies were weaker. Additionally, the positive correlation between memory delay lower frequency lPFC power and contralateral load was not observed for ipsilateral loads. Thus, the independence between the two visual hemifields seen in behavior was reflected in positive, but not the negative, correlations between load and power. As FIGS. 12 and 13 illustrate, the changes in LFP with stimulus load was more complex than this summary; there were differences in the temporal dynamics in effects between brain areas. Next, these effects are quantified and considered in more detail.

Differences in Effects of Stimulus Load by Time and Frequency Band

As FIGS. 12A-12B and 13A-13B indicate, the main effects of stimulus load were seen across two broad frequency bands (lower: 8-50 Hz and higher: 50-100 Hz). When the lower frequencies were separated into standard frequency bands (theta, 4-8 Hz; alpha, 8-12 Hz; beta, 16-30 Hz; low gamma, 30-50 Hz), the pattern of effects in the narrow bands mirrored the broadband effects (i.e., negative correlations in theta through low gamma, positive correlations in high gamma, see Supplementary Figure S1). Thus, for simplicity statistics reported here are statistics computed across the broad bands using the multitaper method (see Materials and Methods).

Figure 14A:
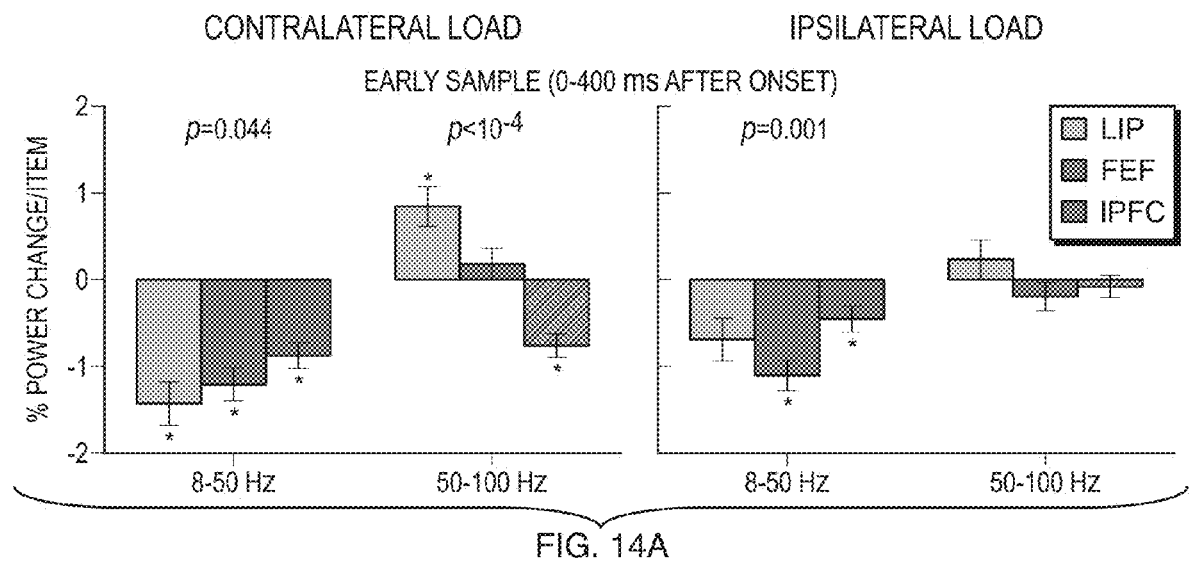
FIGS. 14A-14C illustrate percent power change per contralateral (left) and ipsilateral (right) item by region, grouped by lower frequencies (left bar group) and higher frequencies (right bar group) during the early sample (FIG. 14A), late sample/early delay (FIG. 14B), and late delay (FIG. 14C). Error bars are standard error of the mean. Asterisks indicate significant differences (bootstrap Z-test, $p<0.05$, Holm corrected for 2 bands×3 epochs×3 regions). White hatching indicates significant differences in modulation by ipsilateral and contralateral load (bootstrap Z-test, $p<0.05$, Holm corrected). P-values above bars indicate significant differences between regions (F-test, $p<0.05$).
Figure 14B:
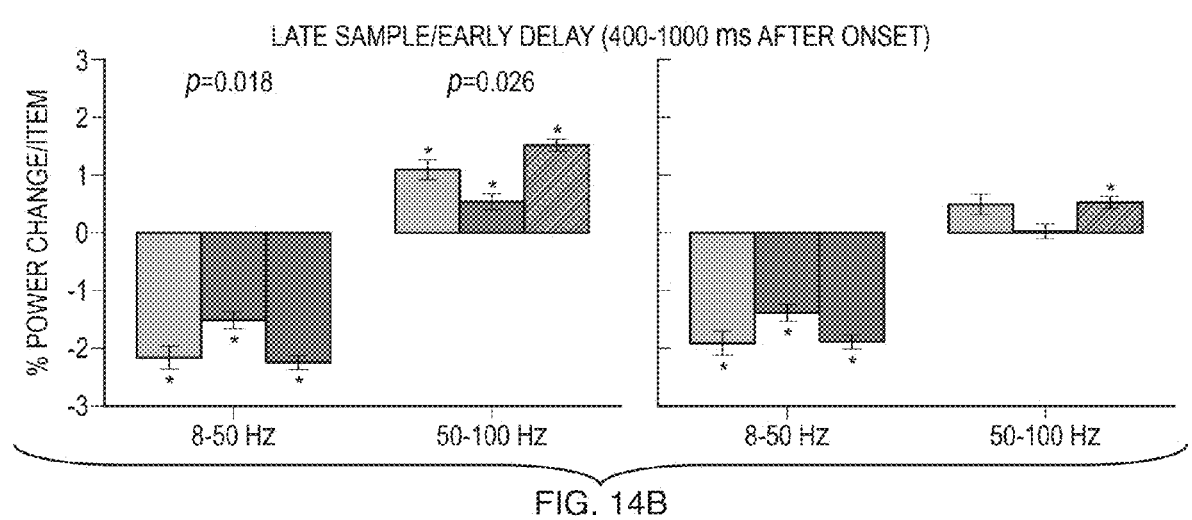
Figure 14C:
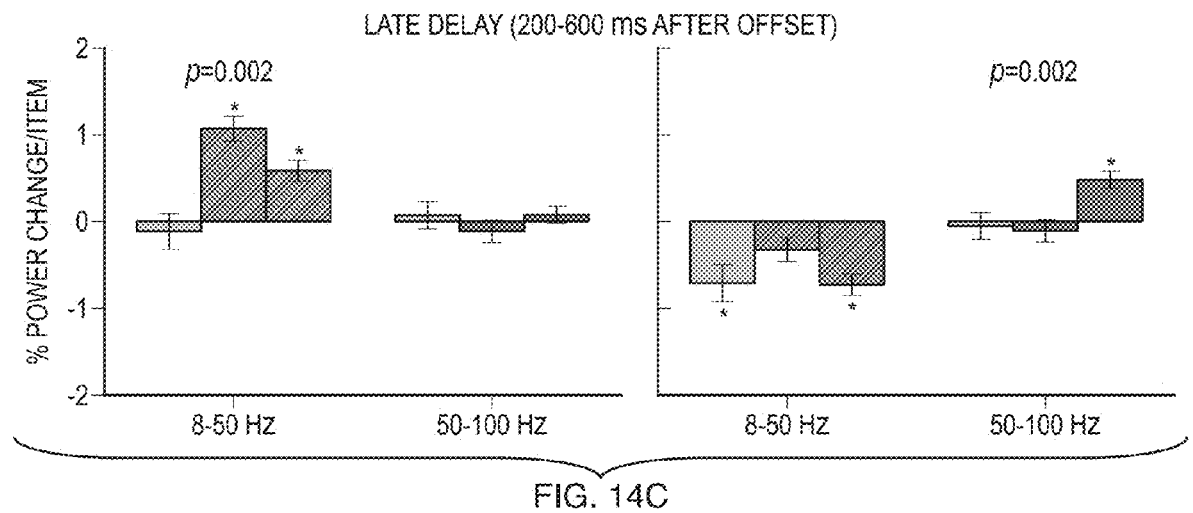
Figure 15:
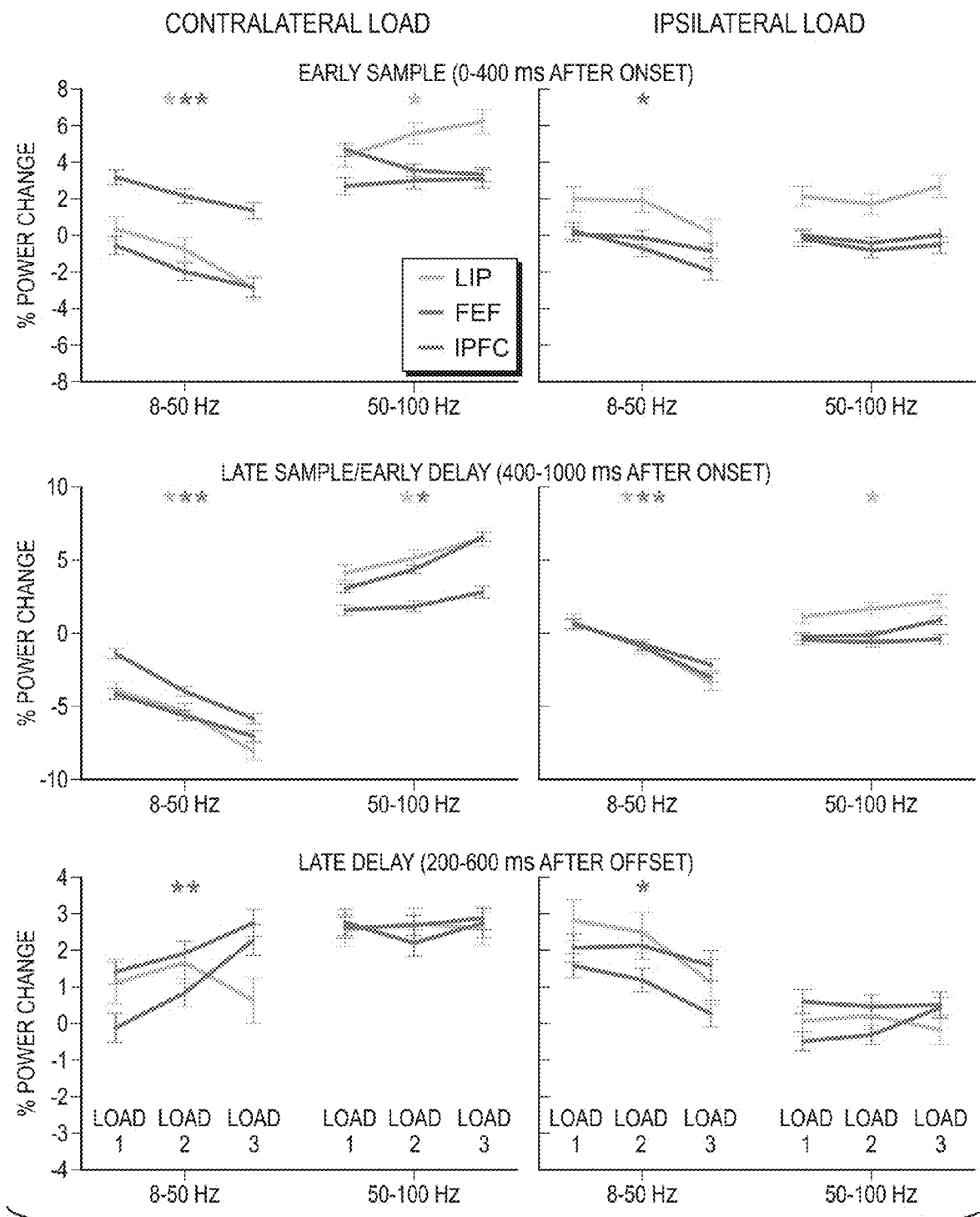
FIG. 15 illustrates percent power change for contralateral loads (left) and ipsilateral loads (right) 1, 2, and 3 relative to load 0, for epochs and frequency bands. Asterisks indicate significance of all pairwise differences for the band, region, and epoch (permutation test, $p<0.05$, Holm corrected for 2 bands×3 epochs×3 regions).

FIGS. 12A-12B and 13A-13B suggest that different load effects were grouped themselves into three distinct time periods, especially in the lPFC. There was an early sample epoch (0-400 ms after sample onset), a late sample/early delay epoch (400-1000 ms after sample onset) and a late delay epoch (1000-1800 ms after sample onset). Therefore, the power across each of these epochs was computed separately. FIGS. 14A-14C plot the average percent change in LFP power per added stimulus for the two broad frequency bands and in each of the three epochs for each brain area (LIP, FEF, lPFC). The asterisks indicate a significant change in power with increasing load. The hatched bars indicate when a given measure in a given brain area showed a significant difference between the effects of contralateral vs. ipsilateral load. Next, the effects in each epoch are considered.

Early Sample Epoch

All three brain areas showed a decrease in low frequency power with increased contralateral stimulus load (LIP: −1.4%/item, $p<10^{-6}$; FEF: −1.2%/item, $p<10^{-8}$; lPFC: −0.9%/item, $p<10^{-6}$; see FIG. 14A). The effects of contralateral load on higher frequency power were mixed. LIP showed a significant positive correlation (0.8%/item, $p=0.004$) and lPFC showed a significant negative correlation with contralateral load (−0.8%/item, $p<10^{-6}$). For ipsilateral loads, there were numerically negative correlations with lower frequencies, but only the FEF and lPFC showed a significant negative correlation with lower frequency power (FEF: −1.1%/item, $p<10^{-6}$; lPFC: −0.5%/item, $p=0.03$). The differences in correlations for contralateral vs. ipsilateral stimulus loads did not reach significance for the lower frequencies. (No bars corresponding to lower frequencies in FIG. 14A are hatched, indicating no difference between contralateral and ipsilateral loads for each area.) In contrast to contralateral loads, none of the areas showed a significant correlation between higher frequencies and ipsilateral load. This difference between the effects of contralateral and ipsilateral load on higher frequencies was significant for the lPFC ($p=0.007$; hatched bars, FIG. 14A). In this way, the higher frequency power was similar to previously reported single-neuron results (Buschman et al. 2011).

Late Sample/Early Delay Epoch

Contralateral stimulus load had different effects on lower versus higher frequencies in all three areas. All three areas showed a significant negative correlation with contralateral load at lower frequencies (LIP: −2.2%/item, $p<10^{-25}$; FEF: −1.5%/item, $p<10^{-22}$; lPFC: −2.2%/item, $p<10^{-79}$; see FIG. 14B) and a significant positive correlation at higher frequencies (LIP: 1.1%/item, $p<10^{-8}$; FEF: 0.5%/item, $p=0.001$; lPFC: 1.5%/item, $p<10^{-45}$). As in the early sample epoch, lower frequency power decreased with ipsilateral load in all three areas (LIP: −1.9%/item, $p<10^{-18}$; FEF: −1.4%/item, $p<10^{-19}$; lPFC: −1.9%/item, $p<10^{-50}$), with weak or no effect on higher frequencies. Only the lPFC showed a small, but significant positive correlation between higher frequency power and ipsilateral load (0.5%/item, $p<10^{-5}$) and it was significantly weaker than the correlation between lPFC higher frequency power and contralateral load (hatched bar in FIG. 14B; $p<10^{-9}$).

Late Delay Epoch

Later in the memory delay, the effects of contralateral load on lower frequency power in the FEF and lPFC reversed relative to earlier in the trial (FIG. 14C). They showed a significant positive (as opposed to negative) correlation between lower frequency power and contralateral load (FEF: 1.1%/item, $p<10^{-11}$; lPFC: 0.6%/item, $p<10^{-4}$). By contrast, there was no effect of contralateral load on higher frequency power. Increased ipsilateral stimulus load continued to produce negative correlations with lower frequency power in LIP (−0.7%/item, $p=0.02$) and lPFC (−0.7%/item, $p<10^{-7}$). This difference between the effects of contralateral and ipsilateral load at lower frequencies was significant for the FEF and lPFC (hatched bars, FIG. 14C; FEF: $p<10^{-9}$; lPFC: $p<10^{-11}$). Ipsilateral load effects on higher frequency power remained weak; only the lPFC showed a positive correlation (0.5%/item, $p<0.0001$).

Do Load Effects Saturate at Behavioral Capacity?

The above sections catalog whether increased stimulus load increased or decreased LFP power. These effects could reflect a strictly monotonic relationship (every added stimulus changes LFP power to a certain degree). Alternatively, there could be a step-like, or threshold, relationship. For example, power could have been constant below a specific load and then increased above it. To test this, the average change from baseline (i.e., no stimulation) was computed for each contralateral and ipsilateral load from one to three stimuli. This is plotted in FIG. 15 for each area and for contralateral and ipsilateral loads. As can be seen, the relationship between stimulus load and power seems mostly monotonic. Each added stimulus produces a similar degree of change in oscillatory power. Note that, even though the animals' performance dropped off beyond two stimuli, adding a third stimulus to the load resulted in further changes in power. The asterisks in FIG. 15 indicate which brain areas showed a strictly monotonic relationship between power and load, i.e., the smallest observed difference in power of any pair of load conditions was larger than would be expected by chance (see Supplementary Methods). In most bands, epochs, and regions where significant modulation of power by load was observed, the effect was strictly monotonic. This was true for all observed low frequency power decreases with contralateral or ipsilateral load in the early sample and late sample/early delay periods, as well as high frequency power increases with contralateral load in LIP during the early sample and in LIP and lPFC during the late sample and early delay. Crucially, in FEF and lPFC, strictly monotonic and seemingly linear effects were present even in the late delay period.

Relationship Between LFP Position and Load Information

In addition to information about stimulus load, LFPs also carried information about stimulus positions. Similar to above, generalized linear models were fit to each electrode, band, and epoch incorporating either load alone or both load and stimulus positions in either the contralateral or ipsilateral hemifields. Based on the difference in these two models, adjusted $R^2$ was computed, a debiased measure of the additional information captured by the model that included stimulus positions similar to $\omega^2$ in linear ANOVA (see Supplementary Methods).

Figure 16:
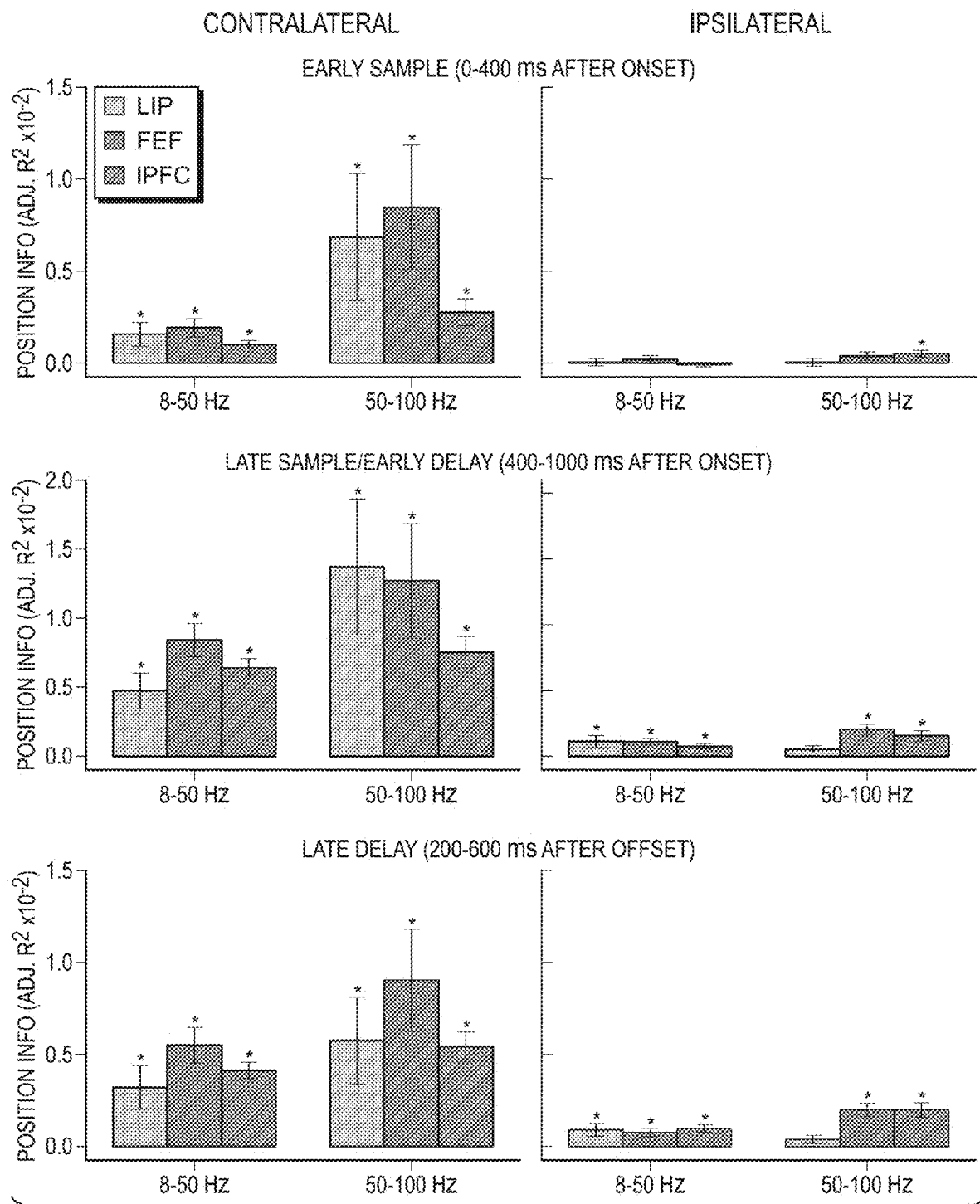
FIG. 16 illustrates comparison of position information (adjusted $R^2$) for contralateral and ipsilateral stimuli. Error bars are standard error of the mean. Asterisks indicate significant information (non-parametric bootstrap test, $p<0.05$, Holm corrected for 2 bands×3 epochs×3 regions). White hatching indicates significant differences in modulation by ipsilateral and contralateral load (non-parametric paired bootstrap test, $p<0.05$, Holm corrected).

In all bands, epochs, and regions, significant information about stimulus position was present in LFP power (all $p<0.0003$, non-parametric bootstrap test, Holm-corrected; FIG. 16). Additionally, a small amount of information about ipsilaterally presented stimuli was present in low frequency power in the late sample/early delay period and late delay periods in all regions and at high frequency power in FEF and lPFC. However, the amount of information about contralaterally presented stimuli was substantially greater in all bands, frequencies, and epochs (all $p<0.005$, paired non-parametric bootstrap test, Holm-corrected).

Figure 17:
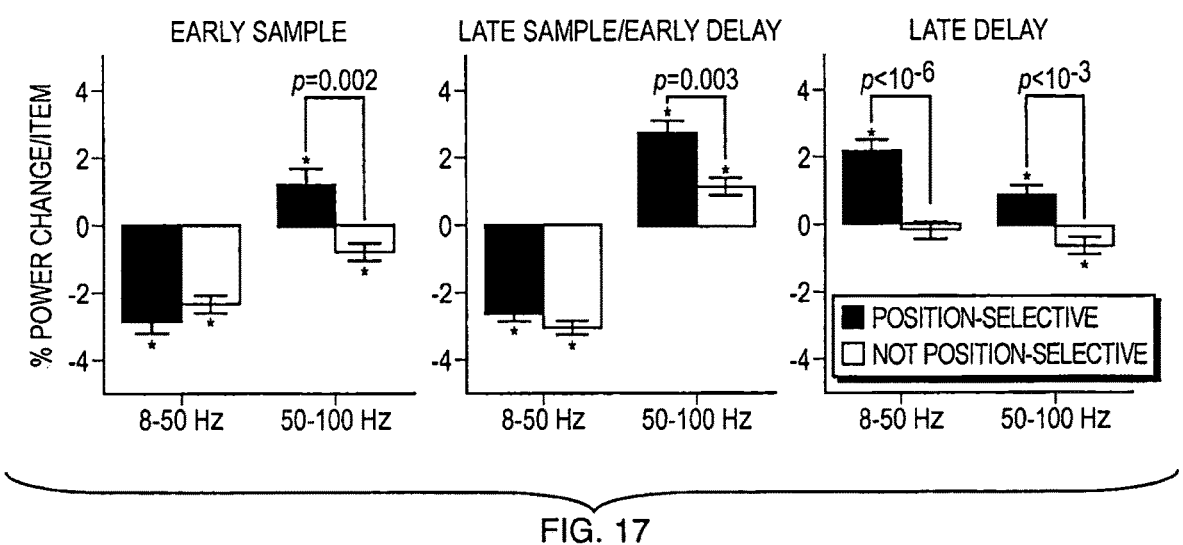
FIG. 17 illustrates percent power change per contralateral item for position-selective and non-position-selective electrodes. Asterisks indicate significant modulation by load (one sample t-test, $p<0.05$, Holm corrected for 2 bands×3 epochs). P-values above bars indicate significant differences between position-selective and non-position-selective electrodes (unequal variance t-test, $p<0.05$, Holm corrected).

The modulation of power by load reported above could reflect either position-specific or position-invariant effects. If power in a given electrode increased or decreased when a stimulus was presented a specific location, then power might also increase or decrease with load, since any given stimulus is more likely to be present at higher loads than at lower loads. Alternatively, the load effects may reflect global changes in power, i.e., even electrodes that do not carry position information might nonetheless show modulation by load. To distinguish these possibilities, for each frequency band and epoch, this study separately computed the average percent power change per contralateral stimulus for electrodes with and without significant effects of contralateral stimulus position in that epoch and band (F-test, $p<0.05$). To minimize confounds from non-position selective electrodes with low statistical power, electrodes were excluded where neither load nor stimulus position explained any significant variation. Because previous analyses showed similar trends across recorded regions, electrodes were pooled across regions to increase statistical power. Applying the analysis to only frontal (FEF and lPFC) electrodes yielded an identical pattern of significance, as did a test for a significant main effect of position selectivity in a 2×3 ANOVA. There were no significant interactions between the effect of position selectivity and region (all $p>0.15$, Holm-corrected F-test). The results of this analysis are shown in FIG. 17.

In the early sample and late sample/early delay period, lower frequency power decreased with contralateral load in both position-selective and non-selective electrodes (all $p<10^{-9}$, t-test), but the strength of the modulation did not differ (early sample: $p=0.34$ [0.26 uncorrected]; late sample: $p=0.34$ [0.17 uncorrected]; unequal variance t-test with Holm correction). Differences were present at higher frequencies. In the early sample period, power in position-selective electrodes increased with contralateral load (1.2%/item, $p=0.04$, one-sample t-test with Holm correction), whereas power in non-position-selective electrodes decreased with load (−0.8%/item, $p=0.01$; difference: $p=0.002$, unequal variance t-test with Holm correction). In the late sample/early delay period, higher frequency power in both position-selective and non-position-selective electrodes increased with load (position-selective: 2.7%/item, $p<10^{-10}$; non-position-selective: 1.1%/item, $p=0.0004$), but position-selective electrodes showed a stronger average modulation ($p=0.003$). Thus, while the mean decrease in lower frequency power with load in the sample period is independent of position selectivity, the mean increase in higher frequency power with load appears to be driven largely by position-selective electrodes. In the late delay period, lower frequency power in position-selective electrodes increased with load (2.2%/item, $p<10^{-9}$). Non-position-selective electrodes showed no average modulation (−0.16%/item, $p=0.5$; difference: $p<10^{-6}$). Since these electrodes were selected on the basis of the presence of power or load effects, it is thought that the individual channel effects average to zero over the recorded population. Thus, like the increase in higher frequency power during the sample period, the mean increase in lower frequency power with load in the late delay period appears to be due to position-selective electrodes. Higher frequency power increased with load for position-selective electrodes (0.9%/item, p=0.02) and decreased with load for non-position-selective electrodes (−0.6%/item, p=0.03; difference: $p<10^{-3}$). This relationship between load and stimulus position effects suggests that the effects of load mostly occur in neuron populations that process bottom-up information about the stimuli (see Discussion).

Effects of Stimulus Load on LFP Synchrony

The above analyses focused on changes in oscillatory power with stimulus load. Next, it is examined whether stimulus load affected the synchrony of LFP signals between electrodes within and across brain areas. Total coherence values across all trials were computed, and single trial surrogate coherence values constructed for each trial as the difference between these total coherence values and coherence values based on all trials except the trial of interest. Then, the correlation between LFP synchrony and load was measured as the correlation between these single trial coherence surrogates and contralateral or ipsilateral load in that trial (see Materials and Methods).

Figure 18:
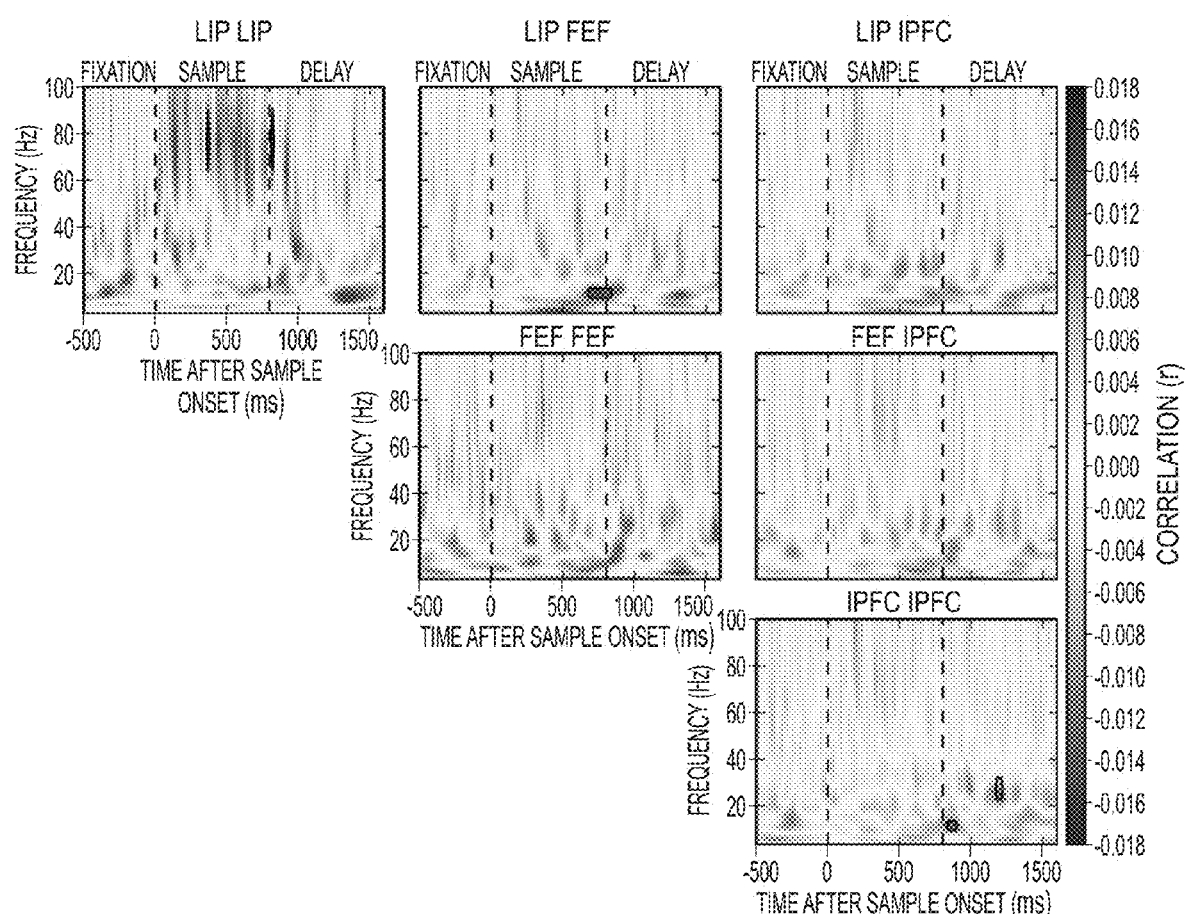
FIG. 18 illustrates correlation of single trial coherence surrogates with contralateral load. Boxes indicate significant modulations (bootstrap Z-test, $p<0.05$, Holm corrected for 22 frequencies×211 time points).
Figure 19:
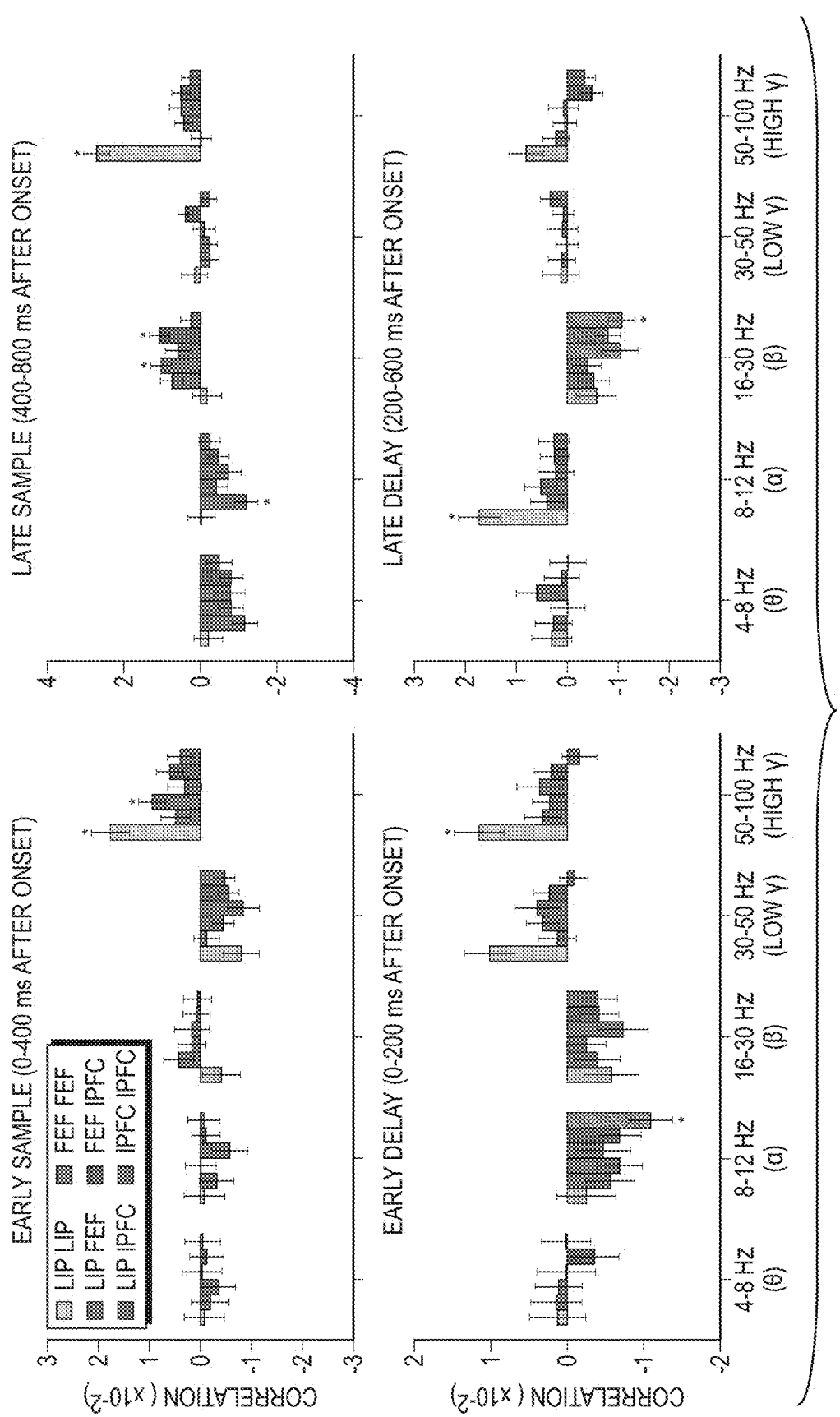
FIG. 19 illustrates correlation of single trial coherence surrogates with contralateral load for frequency bands and epochs. Asterisks indicate significant differences (bootstrap Z-test, $p<0.05$, Holm corrected for 5 bands×4 epochs×6 region pairs). White hatching indicates significant differences in modulation by ipsilateral and contralateral load (bootstrap Z-test, p<0.05, Holm corrected).

FIG. 18 shows the correlation between LFP synchrony and contralateral stimulus load as a function of frequency and time during the trial (see Materials and Methods). There was little, if any, change in synchrony with ipsilateral load (Supplementary Figures S2 and S3). FIG. 19 shows the effects of load on synchrony for the standard frequency bands (theta, alpha, beta, low gamma, and high gamma). Summarized here are the significant effects using the same higher/lower frequency classifications as used for LFP power.

During sample presentation and shortly after, increases in contralateral load increased higher frequency LFP synchrony within LIP (early sample: r=0.017, p=0.0002, bootstrap Z-test, Holm-corrected; late sample: r=0.023, $p<10^{-12}$; early delay: r=0.012, p=0.04; FIGS. 18 and 19) and between LIP and lPFC (only in the early sample, r=0.009, p=0.049). In the late sample epoch, increased contralateral load significantly increased beta synchrony between LIP and lPFC (r=0.010, p=0.02) and between the FEF and lPFC (r=0.011, p=0.004). (While these cross-region effects did not achieve significance in the time-localized analysis in FIG. 18, they are apparent in the epoched analysis in FIG. 19.). In the late delay, beta synchrony within the lPFC instead decreased with contralateral load (r=−0.011, p=0.004). Additionally, there were significant decreases in alpha synchrony with contralateral load between LIP and FEF in the late sample (r=−0.012, p=0.02) and within the lPFC in the early delay (r=−0.011, p=0.02), and an increase in alpha synchrony with contralateral load within LIP in the late delay (r=0.017, p=0.002). As noted above, there were few changes in synchrony with ipsilateral load. There was only a decrease in alpha synchrony in the late sample period (r=−0.012, p=0.009, see Supplementary Figures S2 and S3).

Synchrony effects were generally fewer and smaller than the effects of load on LFP power. Nonetheless, the process described here was able to detect that the effects of contralateral load on LFP synchrony in the sample period had a monotonically increasing relationship with contralateral load. Supplementary Figure S4 shows the difference in pairwise phase consistency between trials with contralateral loads 1, 2, and 3 and zero contralateral load trials for each region pair, band, and epoch. Significance was determined using the same permutation test as in the test for monotonicity of power changes above. Synchrony within LIP increased monotonically with load in the higher frequencies in the early and late sample periods. Synchrony between LIP and lPFC increased monotonically with contralateral load in the beta band in the late sample period. Significant monotonic effects were not seen in other bands after the multiple comparison correction.

Discussion

Effects of different stimulus loads were tested in three brain areas known to be important for visual attention and working memory, the lateral prefrontal cortex (lPFC), the frontal eye fields (FEF) and the lateral intraparietal area (LIP). Previously, Buschman et al. reported the single neuron correlates of stimulus load (Buschman et al. 2011). Reported here are the effects of load on oscillatory dynamics (power and synchrony) of local field potentials (LFPs).

During stimulus presentation, there were decreases in lower frequency (8-50 Hz) LFP power with increases in contralateral and ipsilateral stimulus load. However, higher frequency (50-100 Hz) LFP power increased only with contralateral stimulus load. Contralateral load also (briefly) increased lower frequency (16-50 Hz, encompassing beta and low gamma) power in the middle of the memory delay. This is relevant because the monkeys showed behavioral evidence of separate visual working memory capacities in each hemifield. This predicts that the neural effects of load tied most directly to behavior would be limited to the contralateral field. Synchrony measures are naturally noisier than measures of power but the effects of load on synchrony generally matched effects on power. The exceptions were in the beta band where there was an inverse relationship between stimulus load and synchrony. Beta synchrony (16-30 Hz) increased with stimulus load during the sample presentation (when beta power decreased) and decreased during the delay (when beta power increased). Finally, it was found that even after the monkeys' behavioral capacity had been reached, increases in stimulus load continued to affect oscillatory power.

The present results coincide with previous reports of changes in LFP power in multiple item working memory tasks. Lara and Wallis (2014) also found that in the lPFC, high gamma power increased and beta power decreased during stimulus presentation, while beta power increased during a memory delay. While they did not explicitly compare power in one-item and two-item trials, the effects appear to be stronger in the two-item trials, consistent with the present findings that power in these bands and epochs scales with load. Palva et al. (2011) analyzed MEG and EEG power during a multiple item working memory task in humans. They reported increases in delay period beta and low gamma power with load that did not saturate at behavioral capacity. However, the same authors report that power increases were associated with strengthened inter-areal synchrony (Palva et al. 2010), which were also observed here during sample presentation, but not in the memory delay. Mitchell and Cusack (Mitchell and Cusack 2011) showed bilateral decreases in induced alpha power immediately following sample presentation in human MEG data, consistent with the present findings during the sample presentation.

Increases in high frequency power accompanied by decreases in lower frequency power have also been reported from a variety of visual attention and perception tasks. Monkey studies of V4 and FEF LFPs have shown that attention towards a stimulus increases higher frequency power and decreases lower frequency power (Fries et al. 2008; Gregoriou et al. 2009, 2014). Human EEG and MEG studies report similar results across a wide range of cortical regions (Siegel et al. 2008; Hipp et al. 2011). The present findings add important details. A dissociation was found between the effects of load on lower versus higher frequency power and their relationship to behavior. During sample presentation, lower frequency power was modulated by both contralateral and ipsilateral load, whereas higher frequency power was modulated more by contralateral load. This reflects the strong contralateral bias in visual cortical processing. It suggests that the effects of load on higher frequencies are more strongly associated with bottom-up processing of visual stimulus information per se. Indeed, stronger higher frequency power changes were found in electrodes that showed selectivity for stimulus location (whereas lower frequency power changes were similar in all electrodes.).

This may be due to previously observed associations between lower and higher frequency oscillations and top-down and bottom-up cortical processing, respectively (Engel et al. 2001; 2007; Engel and Fries 2010; Arnal and Giraud 2012; Bastos et al. 2015). Lower frequency (beta) oscillations have been linked to maintaining the existing cognitive set (Engel and Fries 2010; Buschman et al. 2012) and may help to stabilize working memory representations against disruption during memory delays (Pereira and Wang 2014). The present data support these hypotheses. During sample presentation, higher frequency power increased with contralateral load, especially in electrodes with bottom-up information about stimulus location. The difference in modulation between position-selective and non-position-selective electrodes suggests that higher frequency oscillations reflect bottom-up input from sensory areas. However, since non-position-selective electrodes were also modulated by contralateral load during the late sample/early delay period, albeit more weakly, these oscillations could additionally reflect top-down modulation of cortical areas processing contralateral stimuli. Lower frequency power decreased with load during sample presentation and in all electrodes. This suggests a more global state change such as a broader focusing of attention across more locations. By contrast, during the late delay, lower frequency power instead increased only with contralateral load and only in electrodes with information about stimulus location. Thus, during memory maintenance, beta oscillations may stabilize the working memories in the circuits that carry information about the stimuli.

Note that while beta power decreased during stimulus array presentation, beta synchrony increased. Beta synchrony has been linked to shifts of attention between multiple stimuli (Buschman and Miller, 2009). Thus, the increase in beta synchrony with stimulus load may reflect an increased number of attentional shifts. One possible source for beta signals is the pulvinar, which projects to both prefrontal and parietal cortex (Asanuma et al. 1985), contains units with both ipsilateral and contralateral receptive fields (Bender 1981), and has recently been shown to modulate low frequency oscillations and synchrony in extrastriate visual cortex during attention (Saalmann et al. 2012).

The present results put some constraints on models of how cognitive capacity arises. According to "slot" models, capacity is limited by an individual's specific number of memory slots. Once they are filled, capacity is reached (Luck and Vogel 1997, 2013; Vogel et al. 2001; Ma et al. 2014). Any further increase in stimulus load should have no effect on neural activity; once all the slots are filled no more information can be encoded. By contrast, in flexible resource models information is a like a pool. Increasing stimulus load uses more and more of this pool. Once the pool becomes too thin, behavior can no longer be supported and effective capacity is reached, but increasing load beyond behavioral capacity will continue to draw from the pool and thus continue to affect neural activity (Bays and Husain 2008; Luck and Vogel 2013; Ma et al. 2014). As described above, subjects had a behavioral capacity of between one and two in each hemifield. However, increases in local field potential power were observed with stimulus load between two and three stimuli, indicating that the animals processed information about stimuli above behavioral capacity. While the absence of saturation at capacity during stimulus presentation might relate to purely visual processes, the absence of saturation during the late delay period is more surprising and more difficult to explain with a slot model. Nonetheless, it is possible that the power increase reflects maintenance of more spatial locations, but the capacity bottleneck arises in maintaining color per se. Thus, the present results are consistent with either a resource model or a modified slot model in which information is maintained about positions of unremembered stimuli, but a fixed number of slots are available for object identity information. In sum, the observed increases in high gamma oscillations with increased stimulus load may reflect changes in feed-forward (bottom-up) sensory processing. Decreases in lower frequency oscillations may instead reflect top-down processes such as the allocation of attention and working memory maintenance.

REFERENCES

Arnal L H, Giraud A-L. 2012. Cortical oscillations and sensory predictions. Trends Cogn Sci. 16:390-398.

Asaad W F, Eskandar E N. 2008. A flexible software tool for temporally-precise behavioral control in Matlab. J Neurosci Methods. 174:245-258.

Asanuma C, Andersen R A, Cowan W M. 1985. The thalamic relations of the caudal inferior parietal lobule and the lateral prefrontal cortex in monkeys: Divergent cortical projections from cell clusters in the medial pulvinar nucleus. J Comp Neurol. 241:357-381.

Bastos A M, Vezoli J, Bosman C A, Schoffelen J-M, Oostenveld R, Dowdall J R, De Weerd P, Kennedy H, Fries P. 2015. Visual areas exert feedforward and feedback influences through distinct frequency channels. Neuron. 85:390-401.

Bays P M, Husain Richter M. 2008. Dynamic shifts of limited working memory resources in human vision. Science. 321:851-854.

Bender D B. 1981. Retinotopic organization of macaque pulvinar. J Neurophysiol. 46:672-693.

Buschman T J, Denovellis E L, Diogo C, Bullock D, Miller E K. 2012. Synchronous oscillatory neural ensembles for rules in the prefrontal cortex. Neuron. 76:838-846.

Buschman T J, Miller E K. 2007. Top-down versus bottom-up control of attention in the prefrontal and posterior parietal cortices. Science. 315:1860-1862.

Buschman T J, Siegel M, Roy J E, Miller E K. 2011. Neural substrates of cognitive capacity limitations. Proc Natl Acad Sci. 108:11252-11255.

Engel A K, Fries P. 2010. Beta-band oscillations—signalling the status quo? Curr Opin Neurobiol, Cognitive neuroscience. 20:156-165.

Engel A K, Fries P, Singer W. 2001. Dynamic predictions: Oscillations and synchrony in top-down processing. Nat Rev Neurosci. 2:704-716.

Fries P, Womelsdorf T, Oostenveld R, Desimone R. 2008. The effects of visual stimulation and selective visual attention on rhythmic neuronal synchronization in macaque area V4. J Neurosci. 28:4823-4835.

Gray C M, König P, Engel A K, Singer W. 1989. Oscillatory responses in cat visual cortex exhibit inter-columnar synchronization which reflects global stimulus properties. Nature. 338:334-337.

Gregoriou G G, Gotts S J, Zhou H, Desimone R. 2009. High-Frequency, Long-Range Coupling Between Prefrontal and Visual Cortex During Attention. Science. 324:1207-1210.

Gregoriou G G, Rossi A F, Ungerleider L G, Desimone R. 2014. Lesions of prefrontal cortex reduce attentional modulation of neuronal responses and synchrony in V4. Nat Neurosci. 17:1003-1011.

Hipp J F, Engel A K, Siegel M. 2011. Oscillatory synchronization in large-scale cortical networks predicts perception. Neuron. 69:387-396.

Howard M W, Rizzuto D S, Caplan J B, Madsen J R, Lisman J, Aschenbrenner-Scheibe R, Schulze-Bonhage A, Kahana M J. 2003. Gamma oscillations correlate with working memory load in humans. Cereb Cortex. 13:1369-1374.

Ikkai A, McCollough A W, Vogel E K. 2010. Contralateral delay activity provides a neural measure of the number of representations in visual working memory. J Neurophysiol. 103:1963-1968.

Jensen O, Tesche C D. 2002. Frontal theta activity in humans increases with memory load in a working memory task. Eur J Neurosci. 15:1395-1399.

Kowalska D M, Bachevalier J, Mishkin M. 1991. The role of the inferior prefrontal convexity in performance of delayed nonmatching-to-sample. Neuropsychologia. 29:583-600.

Lara A H, Wallis J D. 2014. Executive control processes underlying multi-item working memory. Nat Neurosci. advance online publication.

Li C-SR, Mazzoni P, Andersen R A. 1999. Effect of reversible inactivation of macaque lateral intraparietal area on visual and memory saccades. J Neurophysiol. 81:1827-1838.

Linden D E J, Bittner R A, Muckli L, Waltz J A, Kriegeskorte N, Goebel R, Singer W, Munk M H J. 2003. Cortical capacity constraints for visual working memory: dissociation of fMRI load effects in a fronto-parietal network. NeuroImage. 20:1518-1530.

Lisman J E, Idiart M A P. 1995. Storage of 7+−2 short-term memories in oscillatory subcycles. Science, 3. 267:1512-1515.

Luck S J, Vogel E K. 1997. The capacity of visual working memory for features and conjunctions. Nature. 390:279-280.

Luck S J, Vogel E K. 2013. Visual working memory capacity: from psychophysics and neurobiology to individual differences. Trends Cogn Sci. 17:391-400.

Lundqvist M, Herman P, Lansner A. 2011. Theta and gamma power increases and alpha/beta power decreases with memory load in an attractor network model. J Cogn Neurosci. 23:3008-3020.

Luria R, Vogel E K. 2011. Shape and color conjunction stimuli are represented as bound objects in visual working memory. Neuropsychologia, Attention and Short-Term Memory. 49:1632-1639.

Matsushima A, Tanaka M. 2014. Different neuronal computations of spatial working memory for multiple locations within versus across visual hemifields. J Neurosci. 34:5621-5626.

Ma W J, Husain M, Bays P M. 2014. Changing concepts of working memory. Nat Neurosci. 17:347-356.

McCollough A W, Machizawa M G, Vogel E K. 2007. Electrophysiological measures of maintaining representations in visual working memory. Cortex. 43:77-94.

Meltzer J A, Zaveri H P, Goncharova I I, Distasio M M, Papademetris X, Spencer S S, Spencer D D, Constable R T. 2008. Effects of Working Memory Load on Oscillatory Power in Human Intracranial EEG. Cereb Cortex. 18:1843-1855.

Mitchell D J, Cusack R. 2011. The temporal evolution of electromagnetic markers sensitive to the capacity limits of visual short-term memory. Front Hum Neurosci. 5:18.

Mittlbock M, Heinzl H. 2002. Measures of explained variation in gamma regression models. Commun Stat-Simul Comput. 31:61-73.

Palva J M, Monto S, Kulashekhar S, Palva S. 2010. Neuronal synchrony reveals working memory networks and predicts individual memory capacity. Proc Natl Acad Sci. 107:7580-7585.

Palva S, Kulashekhar S, Hamalainen M, Palva J M. 2011. Localization of cortical phase and amplitude dynamics during visual working memory encoding and retention. J Neurosci. 31:5013-5025.

Passingham R. 1975. Delayed matching after selective prefrontal lesions in monkeys (*Macaca mulatta*). Brain Res. 92:89-102.

Pereira J, Wang X-J. 2014. A tradeoff between accuracy and flexibility in a working memory circuit endowed with slow feedback mechanisms. Cereb Cortex. in press: bhu202.

Richter C G, Thompson W H, Bosman C A, Fries P. 2015. A jackknife approach to quantifying single-trial correlation between covariance-based metrics undefined on a single-trial basis. NeuroImage. 114:57-70.

Saalmann Y B, Pinsk M A, Wang L, Li X, Kastner S. 2012. The Pulvinar Regulates Information Transmission Between Cortical Areas Based on Attention Demands. Science. 337:753-756.

Salazar R F, Dotson N M, Bressler S L, Gray C M. 2012. Content-specific fronto-parietal synchronization during visual working memory. Science. 338:1097-1100.

Sawaguchi T, Goldman-Rakic P S. 1991. D1 dopamine receptors in prefrontal cortex: involvement in working memory. Science. 251:947-950.

Siegel M, Donner T H, Oostenveld R, Fries P, Engel A K. 2008. Neuronal synchronization along the dorsal visual pathway reflects the focus of spatial attention. Neuron. 60:709-719.

Todd J J, Marois R. 2004. Capacity limit of visual short-term memory in human posterior parietal cortex. Nature. 428:751.

Todd J J, Marois R. 2005. Posterior parietal cortex activity predicts individual differences in visual short-term memory capacity. Cogn Affect Behav Neurosci. 5:144-155.

Vinck M, van Wingerden M, Womelsdorf T, Fries P, Pennartz C M A. 2010. The pairwise phase consistency: A bias-free measure of rhythmic neuronal synchronization. NeuroImage. 51:112-122.

Vogel E K, Machizawa M G. 2004. Neural activity predicts individual differences in visual working memory capacity. Nature. 428:748-751.

Vogel E K, McCollough A W, Machizawa M G. 2005. Neural measures reveal individual differences in controlling access to working memory. Nature. 438:500-503.

Vogel E K, Woodman G F, Luck S J. 2001. Storage of features, conjunctions, and objects in visual working memory. J Exp Psychol Hum Percept Perform. 27:92-114.

Voytek B, Knight R T. 2010. Prefrontal cortex and basal ganglia contributions to visual working memory. Proc Natl Acad Sci. 107:18167-18172.

Womelsdorf T, Fries P, Mitra P P, Desimone R. 2006. Gamma-band synchronization in visual cortex predicts speed of change detection. Nature. 439:733.

Simon Kornblith, Timothy J. Buschman, Earl K. Miller; Stimulus Load and Oscillatory Activity in Higher Cortex, Cerebral Cortex, Volume 26, Issue 9, 1 Sep. 2016, Pages 3772-3784, published online 18 Aug. 2015, doi.org.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method for customizing a controller in a display system, the method comprising:
    displaying, at a display device, a visual stimulus to a subject at at least one known location relative to the subject's eye gaze;
    measuring brain activity of the subject's left and right brain hemispheres in response to the subject's viewing of the stimulus, the measuring including measuring local field potentials, the brain activity having a frequency component associated therewith;
    processing the measured brain activity to determine a frequency-dependent metric of the brain activity, the processing including computing oscillatory power of the measured local field potentials;
    assessing independent cognitive capacities of the subject's left and right brain hemispheres based on the frequency-dependent metric of the brain activity, the assessing including comparing the computed oscillatory power to a threshold value; and
    adjusting a function of the controller in the display system to change a property of the stimulus displayed or other visual representations displayed at the display device according to the assessment of the independent cognitive capacities, the adjusting including taking a compensatory action based on a result of the comparison, the compensatory action including, for a given brain hemisphere, modulating stimulus load to the contralateral visual hemifield.

2. The method of claim 1, wherein the function changes the stimulus load by modulating at least one of a number of objects or a complexity of objects in the stimulus displayed.

3. The method of claim 1, further comprising monitoring the subject's eye gaze by tracking the subject's eye position, the stimulus being displayed based on the subject's eye gaze.

4. The method of claim 3, further comprising ensuring alignment of the subject's eye gaze with a fixation point during the measuring of the brain activity.

5. The method of claim 4, wherein ensuring alignment includes providing feedback to the subject.

6. The method of claim 4, wherein ensuring alignment includes moving the stimulus displayed in response to the subject's eye gaze.

7. The method of claim 1, wherein measuring the brain activity includes measuring at least one of EEG signals, MEG signals, infrared signals recorded from the subject's scalp, BOLD signals from fMRI, and blood volume changes from functional ultrasound.

8. The method of claim 1, wherein the oscillatory power is computed for selected frequency bands, the frequency bands including a lower frequency band of about 8-50 Hz and a higher frequency band of about 50-200 Hz.

9. The method of claim 8, further comprising computing a ratio of oscillatory power in the higher frequency band to oscillatory power in the lower frequency band.

10. The method of claim 1, further comprising assessing the subject's current level of cognitive function by determining overall cognitive capacity of the subject as a function of the independent cognitive capacities.

11. The method of claim 10, wherein assessing the subject's current level of cognitive function includes comparing the determined overall cognitive capacity to a baseline capacity.

12. The method of claim 1, further comprising changing a stimulus load of the stimulus or other visual representations displayed at a region of the display device aligned with a visual hemifield according to the frequency-dependent metric of the brain activity in the subject's contralateral brain hemisphere.

13. A dynamic display system comprising:
    a display device to display a visual stimulus to a subject;
    a controller coupled to the display device, the controller causing the display device to display the stimulus at at least one known location relative to the subject's eye gaze;
    a detector to measure brain activity of the subject's left and right brain hemispheres in response to the subject's viewing of the stimulus, the measuring including measuring local field potentials, the brain activity having a frequency component associated therewith; and
    at least one processor coupled to the detector and the controller, the processor configured to:
    process the measured brain activity to determine a frequency-dependent metric of the brain activity, the processing including computing oscillatory power of the measured local field potentials;
    assess independent cognitive capacities of the subject's left and right brain hemispheres based on the frequency-dependent metric of the brain activity, the assessing including comparing the computed oscillatory power to a threshold value; and
    adjust a function of the controller in the display system to change a property of the stimulus displayed or other visual representations displayed at the display device according to the assessment of the independent cognitive capacities, the adjusting including taking a compensatory action based on a result of the comparison, the compensatory action including, for a given brain hemisphere, modulating stimulus load to the contralateral visual hemifield.

14. The system of claim 13, wherein the function changes the stimulus load by modulating at least one of a number of objects or a complexity of objects in the stimulus displayed.

15. The system of claim 13, further comprising a camera configured to track the subject's eye position to monitor the subject's eye gaze, the stimulus being displayed based on the subject's eye gaze.

16. The system of claim 13, wherein the processor is configured to compute oscillatory power for selected frequency bands, the frequency bands including a lower frequency band of about 8-50 Hz and a higher frequency band of about 50-200 Hz.

17. The system of claim 13, further including at least one filter to process the measured brain activity by selecting for at least one frequency band of the measured brain activity, the at least one filter being implemented in the detector, the processor, or both.

18. The system of claim 13, wherein the at least one processor is further configured to change a stimulus load of the stimulus or other visual representations displayed at a region of the display device aligned with a visual hemifield according to the frequency-dependent metric of the brain activity in the subject's contralateral brain hemisphere.

* * * * *